(12) United States Patent
Sakai

(10) Patent No.: US 7,465,541 B1
(45) Date of Patent: Dec. 16, 2008

(54) VITAMIN D$_3$-RESPONSIVE SEQUENCES LOCATED 5'-UPSTREAM OF P27/$^{KIP\ 1}$ GENE AND METHODS OF SCREENING FOR PHARMACEUTICAL AGENTS USING THE SEQUENCES

(75) Inventor: Toshiyuki Sakai, Kyoto (JP)

(73) Assignees: Toshiyuki Sakai, Kyoto (JP); Chungai Seiyaku Kabushiki Kaisha, Tokyo (JP)

( * ) Notice: Subject to any disclaimer, the term of this patent is extended or adjusted under 35 U.S.C. 154(b) by 341 days.

(21) Appl. No.: 10/181,614

(22) PCT Filed: Jul. 21, 2000

(86) PCT No.: PCT/JP00/04896

§ 371 (c)(1),
(2), (4) Date: Nov. 15, 2002

(87) PCT Pub. No.: WO01/53402

PCT Pub. Date: Jul. 26, 2001

(30) Foreign Application Priority Data

Jan. 21, 2000 (JP) .............................. 2000-017809

(51) Int. Cl.
C12N 15/85 (2006.01)
C12N 15/63 (2006.01)
C12N 5/10 (2006.01)
C12Q 1/68 (2006.01)
A61K 31/593 (2006.01)

(52) U.S. Cl. .................. 435/6; 435/7.1; 435/320.1; 435/325; 536/23.2; 536/24.1

(58) Field of Classification Search ............... 435/320.1; 536/23.1, 24.1
See application file for complete search history.

(56) References Cited

U.S. PATENT DOCUMENTS

| | | | |
|---|---|---|---|
| 5,807,740 A | 9/1998 | Amaral et al. | |
| 6,048,693 A | 4/2000 | Bitter | |
| 6,225,112 B1 | 5/2001 | Sakai et al. | |
| 6,489,104 B1 * | 12/2002 | Sakai et al. .................. | 435/6 |
| 6,524,796 B1 * | 2/2003 | Sakai et al. .................. | 435/6 |
| 6,623,925 B1 * | 9/2003 | Sakai et al. .................. | 435/6 |

OTHER PUBLICATIONS

Zou et al., Journal of Biological Chemistry, 1997, vol. 272, No. 30, pp. 19027-19034.*

Akiyama et al., "G, Phase Accumulation Induced by UCN-01 Is Associated with Dephosphorylation of Rb and CDK2 Proteins well as induction of CDK Inhibitor p21/Cip1/WAF1/Sdh1 in p53-Mutated Human Epidermoid Carcinoma A431 Cells," *Cancer Research*, 57:1495-1501 (1997).

Datto et al., "Functional Analysis of the Transforming Growth Factor β Responsive Elements in the WAF1/Clpp21/p21 Promoter," *Journal of Biological Chemistry* 270:28623-28628 (1995).

Ito et al., "Two Short Sequences Have Positive Effects on the Human p27$^{Kip1}$ Gene Transcription," *Gene* 228:93-100 (1999).

Kwon et al., "Charaterization of the Murine Cyclin-Depndent Kinase Inhibitor Gene p27$^{Kip1}$" *Gebe* 180:113-120 (1996).

Liu et al., "Transcriptional Activation of the Cdk Inhibitor p21 by Vitamin D$_3$ Leads to the Induced Differentiation of the Myelomonocytic Cell Line U937" *Genes Dev.* 10:142-153 (1996).

Minami et al., "Molecular Cloning and Characterization of the Human p27$^{Kip1}$ Gene Promoter," *FEBS Letters* 411:1-6 (1997).

Tomoda et al., "Degradation of the Cyclin-Dependent-Kinase Inhibitor p27$^{Kip1}$ Is Instigated by Jab 1," *Nature* 398:160-165 (1999).

Toyoshima and Hunter,"p27, a Novel Inhibitor of G1 Cyclin-Cdk Protein Kinase Activity, Is Related to p21," *Cell* 78:67-74 (1994).

Vlach et al., "Phosphorylation-Dependent Degradation of the Cyclin-Dependent Kinase Inhibitor p27$^{Kip1}$," *The EMBO Journal* 16:5334-5344 (1997).

Zhang and Lin, "Molecular Characterization of the Cyclin-Dependent Kinase Inhibitor p27 Promoter," *Biochimica et Biophysica Acta* 1353:307-317 (1997).

Inoue et al., "Sp1 and NF-Y Synergistically Mediate the Effect of Vitamin D$_3$ in the p27$^{Kip1}$ Gene Promoter that Lacks Vitamin D Response Elements," *The Journal of Biological Chemistry* 274:32309-32317 (1999).

Kamiyama et al., "The Ubiquitous Transcription Factor NF-Y Positively Regulates the Transcription of Human p27$^{Kip1}$ Through a CCAAT Box Located in the 5'-Upstream Region of the p27$^{Kip1}$ Gene," *FEBS Letters* 455:281-285 (1999).

* cited by examiner

*Primary Examiner*—David Guzo
(74) *Attorney, Agent, or Firm*—Clark & Elbing LLP

(57) ABSTRACT

A 44-bp region that confers vitamin D$_3$-responsiveness to the human p27$^{Kip1}$ promoter in the human p27$^{Kip1}$ transcriptional regulatory mechanism was revealed. This region also conferred vitamin D$_3$-responsiveness to a heterogenous promoter. Moreover, it was found that vitamin D$_3$ enhances the binding between the CCAAT box existing in the region and the NF-Y protein and also the binding between the Sp1 sequence (also existing in the region) and the Sp1 protein, thus inducing human p27$^{Kip1}$ transcription. Also revealed were methods of screening for pharmaceutical agents that regulate the expression of the p27$^{Kip1}$ gene using these molecular mechanisms.

14 Claims, 16 Drawing Sheets

Relative luciferase activity (RLU/ μg protein)

VITAMIN D₃-RESPONSIVE SEQUENCES LOCATED 5'-UPSTREAM OF P27/KIP 1 GENE AND METHODS OF SCREENING FOR PHARMACEUTICAL AGENTS USING THE SEQUENCES

CROSS-REFERENCES TO RELATED APPLICATIONS

This application is the U.S. national phase of PCT/JP00/04896, filed Jul. 21, 2000, which, in turn, claims benefit of Japanese patent application number JP 2000/17809, filed Jan. 21, 2000.

TECHNICAL FIELD

This invention relates to vitamin D₃-responsive sequences located in the 5' regulatory region of the $p27^{Kip1}$ gene and screening methods for pharmaceutical agents using the sequences.

BACKGROUND ART $p27^{Kip1}$ is an inhibitor of many cyclin dependent kinases (cdk) and is believed to be essential for the strict control of the cell cycle, both in vivo and in vitro. Human tumor cells usually do not have mutations in the $p27^{Kip1}$ gene (Ponce-Castaneda, M. V. et al. (1995) Cancer Res., 55, 1211-1214), but they often have very low levels of the $p27^{Kip1}$ protein. The low levels of the protein correlate with low survival rates of breast cancer (Porter, P. L. et al, (1997) Nat. Med., 3, 222-225; Loda, M. et al. (1997) Nat. Med., 3, 231-234), lung cancer (Esposito, V. et al. (1997) Cancer Res., 57, 3381-3385), prostate cancer (Yang, R. M. et al. (1998) J. Urol., 159, 941-945), and stomach cancer patients (Yasui, W. et al. (1997) Jpn. J. Cancer Res., 88.625-629). Moreover, a recent study showed that $p27^{Kip1}$ was haplo-insufficient for tumor suppression (Fero, M. L. et al. (1998) Nature, 396, 177-180). This means that the tendency to form a tumor is increased by inactivation of one of the alleles or by a decrease in the expression of the protein. One of the most important strategies in cancer treatment is to revive the expression of tumor suppresser proteins. Therefore, $p27^{Kip1}$ may be a useful molecule for cancer treatment. Recent research indicates that $p27^{Kip1}$ mRNA levels are increased when neuroblastoma cells are incubated with a thyroid hormone, when embryonic carcinoma cells are incubated with retinoic acid, or when stomach cancer cells are incubated with interferon-β (Perez-Juste, G. and Aranda, A., (1999) J. Biol. Chem., 274, 5026-5031; Kawasaki, H. et al. (1998) Nature, 393, 284-289; Kuniyasu, H. et al. (1997) Cell Growth Differ., 8, 47-52). These results indicate that stability and levels of the $p27^{Kip1}$ protein are increased by the up-regulation of $p27^{Kip1}$ transcription. Therefore, it is assumed that regulation of $p27^{Kip1}$ transcription has a more general importance. However, very little is known about the mechanism that regulates $p27^{Kip1}$ transcription. The present inventors previously cloned the promoter region of the human $p27^{Kip1}$ gene and discovered that the region between position −774 and −435 (relative to the transcription initiation site) was vital for promoter activity (Minami, S. et al. (997) FEBS Lett., 411, 1-6; Unexamined Published Japanese Patent Application No. (JP-A) Hei 11-137251).

1,25-dihydroxyvitamin D₃ is not only a major regulator of mineral homeostasis but is also a potent modulator of differentiation in several types of cells, including monoblastic cells and osteoblasts (Minghetti, P. P. and Norman, A. W., (1988) FASEB J., 2, 3043-3053). Recent studies have revealed that the cdk inhibitors, $p21^{Cip1}$ and $p27^{Kip1}$, function as molecular switches that facilitate the vitamin D₃-induced differentiation of the U937 myeloid leukemic cell line. These genes are regulated both at the transcriptional level and the post-transcriptional level by vitamin D₃ during the early stages of this differentiation process (Liu, M. et al. (1996) Genes Dev., 10, 142-153). Vitamin D₃ transduces its signal to the nucleus directly, mainly through a regulatable DNA-binding transcription factor, the vitamin D receptor (VDR) (Evans, R. M., (1988) Science, 240, 889-895). Also, ligand-inducible effects on differentiation are initiated through the direct activation of target genes by VDR. In fact, vitamin D₃ induces $p27^{Kip1}$ transcription in a VDR-dependent manner through a functional vitamin D response element (VDRE) in its promoter (Liu, M. et al. (1996) Genes Dev., 10, 142-153). Clarification of the regulatory mechanisms of $p27^{Kip1}$ transcription is not only crucial for the understanding of the molecular mechanisms of vitamin D₃ action and for the understanding of the early processes during monocyte/macrophage differentiation, but is also extremely important for developing a method for tumor suppression through regulation of $p27^{Kip1}$ expression. Although the post-transcriptional regulation of $P_{27}^{Kip1}$ has been studied intensively (Pagano, M. et al. (1995) Science, 269, 682-685; Vlach, J. et al. (1997) EMBO J., 16, 5334-5344; Tomoda, K. et al. (1999) Nature, 398, 160-165), very little is known regarding the transcriptional regulation of the $p27^{Kip1}$ gene.

DISCLOSURE OF THE INVENTION

This invention relates to vitamin D₃ responsive sequences located in the 5' regulatory region of $p27^{Kip1}$ gene and methods of screening for pharmaceutical agents that regulate the expression of the $p27^{Kip1}$ gene using the sequences.

The inventors analyzed sequence elements of the 5' regulatory region of the $p27^{Kip1}$ gene in order to investigate the mechanism that regulates $p27^{Kip1}$ gene transcription.

Specifically, the inventors first performed promoter analysis using a 5' deletion mutant and revealed that the region between position −549 and position −511 located 5' upstream from the $p27^{Kip1}$ gene is necessary to obtain maximum promoter activity (FIG. 1). Moreover, point mutation analysis revealed that both the Sp1 sequence (GGGCGG) and CCAAT box within this region regulate promoter activity (FIG. 2). In particular, the CCAAT box was essential for inducing basal transcriptional activity of the $p27^{Kip1}$ promoter. Gel shift assay using oligonucleotides containing the CCAAT box of the $p27^{Kip1}$ promoter was conducted to screen for transcription factors that bind to the CCAAT box. The results showed that the transcription factor, nuclear factor Y (NF-Y), binds to the CCAAT box, in the $p27^{Kip1}$ promoter (FIGS. 3 and 4). Moreover, coexpression with a NF-Y dominant negative showed that NF-Y directly regulates $p27^{Kip1}$ transcription via the CCAAT box (FIG. 5).

The present inventors also examined the possibility that these sequences detected in the $p27^{Kip1}$ promoter, which play an important role in the translational regulation, may also be involved in vitamin D₃-mediated transcriptional regulation of the $p27^{Kip1}$ gene. The present inventors found no obvious vitamin D response element (VDRE) sequence (5'-RGKT-CANNNRGKTCA-3'; SEQ ID NO:17) within the 3.6 kilobases located in the 5'-flanking region upstream from the translation start site of the human $p27^{Kip1}$ gene. This result suggests that $p27^{Kip1}$ is regulated by mechanisms different from other vitamin D₃ target genes, such as $p21^{Cip1}$ (Liu, M. et al. (1996) Genes Dev., 10, 142-153), c-fos (Schrader, M. et al. (1997) Biochem. Biophys. Res. Commun., 230, 646-651), and osteocalcin (Demay, M. B. et al. (1990) Proc. Natl. Acad. Sci. USA, 87, 369-373). Furthermore, the present inventors speculated that there may be a novel pathway for vitamin $D_3$ induced regulation that does not directly involve VDR/VDRE. Therefore, the inventors analyzed the $p27^{Kip1}$ promoter to identify sequences required for positive regulation of $p27^{Kip1}$ transcription by vitamin $D_3$ and to elucidate a novel mechanism involving vitamin $D_3$ during early stages of cell differentiation induction.

The transcriptional activity of the 3.6 Kb 5'-flanking region of the human $p27^{Kip1}$ gene was examined by transiently transfecting U937 cells with a luciferase reporter construct. The result showed that the transcriptional activity of this construct was induced by vitamin $D_3$ (FIG. 6). Deletion and mutation analysis revealed that both the GGGCGG sequence (−545/−538) and the CCAAT box (−522/−518) were necessary to induce $p27^{Kip1}$ gene expression (FIG. 7). Surprisingly, a 44 base pair region containing both of these sequences (−555 to −512) was sufficient for inducing a positive response to vitamin $D_3$ by even other heterologous promoters in addition to $p27^{Kip1}$ promoter (FIG. 8).

Gel shift assays showed that Sp1 binds to the Sp1 sequence (GGGCGG) and that NF-Y binds to the CCAAT box (FIGS. 9-13). Consistent with the roles of these transcription factors, treatment with vitamin $D_3$ stimulated the DNA binding activities of these factors to each sequence (FIG. 14) and induced a change in one of the NF-Y subunits (FIGS. 15 and 16). It was thought that vitamin $D_3$ stimulates the transcription of the $p27^{Kip1}$ gene by a transcriptional regulation mechanism involving Sp1 and NF-Y (but not the vitamin $D_3$ receptor) during the early stages of U937 cell differentiation.

There have been reports describing vitamin $D_3$-dependent down regulation of transcription independent of VDR (Ezura, Y. et al. (1997) J. Biol. Chem., 272, 29865-29872; Alroy, I. et al. (1995) Mol. Cell. Biol., 15, 5789-5799). For the first time this invention describes a molecular mechanism of vitamin $D_3$-induced transcription that does not require the direct involvement of VDR.

The $p27^{Kip1}$ gene can be an important target for developing a strategy for cancer treatment because of its role in reviving the expression of tumor suppresser proteins (Fero, M. L. et al. (1998) Nature, 396, 177-180). This invention demonstrated that vitamin $D_3$ responsive sequences are located at 5' upstream of the $p27^{Kip1}$ gene. It also demonstrated the interaction between the sequences and NF-Y and Sp1. Thus, the present invention provides a novel effective system to develop pharmaceutical agents that regulate the transcription of the $p27^{Kip1}$ gene. Moreover, it is hoped that the present invention will enable the development of novel gene-regulating chemotherapies and gene-regulating chemoprevention (Sakai, T., (1996) Jpn. J. Hyg., 50, 1036-1046).

This invention is based on the findings described above and provides methods of screening for new pharmaceutical agents using vitamin $D_3$ responsive sequences located at the 5' upstream regulatory region of the $p27^{Kip1}$ gene.

More specifically, the present invention relates to:

(1) a DNA having the activity to give positive vitamin $D_3$ responsiveness to heterologous and homologous promoters, wherein said DNA is selected from the group consisting of:
   (a) the nucleotide sequence from position 3014 to position 3057 of SEQ ID NO: 1;
   (b) a DNA from a non-human organism corresponding to the DNA of (a); and
   (c) a DNA comprising a nucleotide sequence in which one or more nucleotides of the nucleotide sequence of the DNA of (a) or
   (b) has been modified by a substitution, deletion, addition, and/or insertion;

(2) a vector comprising the DNA of (1);

(3) the vector of (2) wherein a reporter gene is operably linked to the downstream of the DNA of (1);

(4) a cell comprising the vector of (2) or (3);

(5) a method of screening for a compound that regulates the expression of $p27^{Kip1}$ gene, wherein the method comprises the steps of:
   (a) contacting a test sample to a cell comprising the vector of (3);
   (b) detecting reporter activity in said cell; and
   (c) selecting a compound that increases or decreases the reporter activity when compared to the activity in the absence of the test sample;

(6) a method of screening for a compound that regulates the expression of $p27^{Kip1}$ gene, wherein the method comprises the steps of:
   (a) contacting NF-Y protein with a DNA comprising (i) a DNA comprising the CCAAT box in the 5' regulatory region of human $p27^{Kip1}$ gene, or (ii) a non-human-derived DNA corresponding to the DNA of (i), in the presence of a test sample;
   (b) detecting binding of NF-Y protein with said DNA; and
   (c) selecting a compound that increases or decreases the binding activity of said DNA with the NF-Y protein when compared to the activity in the absence of the test sample;

(7) a method of screening for a compound that regulates $p27^{Kip1}$ gene expression, wherein said method comprises the steps of:
   (a) contacting the Sp1 protein with a DNA comprising (i) a DNA region comprising the Sp1 sequence in the 5' regulatory region of human $p27^{Kip1}$ gene, or (ii) a non-human-derived DNA corresponding to the DNA region of (i), in the presence of a test sample;
   (b) detecting binding of Sp1 protein with said DNA; and
   (c) selecting a compound having an activity to increase or decrease the binding activity of the DNA with Sp1 protein when compared to the activity in the absence of the test sample;

(8) the method of (6) or (7), wherein the detection is performed using a gel shift assay;

(9) a pharmaceutical agent that enhances the binding of NF-Y protein with the CCAAT box in the 5' regulatory region of human $p27^{Kip1}$ gene, or a corresponding non-human CCAAT box, wherein the pharmaceutical agent comprises vitamin $D_3$, or a derivative thereof, as the active ingredient; and

(10) a pharmaceutical agent that enhances the binding of Sp1 protein with the Sp1 sequence in the 5' regulatory region of the human $p27^{Kip1}$ gene, or a corresponding non-human Sp1 sequence, wherein the pharmaceutical agent comprises vitamin $D_3$, or a derivative thereof, as the active ingredient.

This invention provides vitamin $D_3$ responsive sequences that exist in the 5' regulatory region of $p27^{Kip1}$ gene. Deletion and mutation analyses conducted by the present inventors revealed that both the Sp1 sequence and CCAAT box were necessary for vitamin $D_3$ responsive promoter activity. Surprisingly, it was found that the region comprising these sequences could also bring about a positive response for vitamin $D_3$ even in the case of heterologous promoters. Thus, this invention provides DNA sequences in the 5' regulatory region that confer vitamin $D_3$ responsiveness to heterologous and homologous promoters. Such properties of the vitamin $D_3$ responsive sequences of the present invention enable, for example, vitamin $D_3$-dependent expression of functional proteins by inserting a functional gene behind a heterologous or homologous promoter that contains vitamin $D_3$ responsive sequences. This will be effective when applying the instant invention to gene therapy, etc.

More specifically, the vitamin $D_3$ responsive sequences of this invention are included in the DNA having the nucleotide sequence between position −555 and position −512 (position 3014 to position 3057 in the SEQ ID NO: 1) 5' upstream of the human p27$^{Kip1}$ gene. Another embodiment of the present invention includes non-human DNA sequences corresponding to the above-mentioned DNA, as long as they have an activity to confer a positive vitamin $D_3$ response to a heterologous or homologous promoter. The non-human DNA can be derived from, for example, a mammal such as mouse (5' upstream of the mouse p27$^{Kip1}$ gene is described in Biochim Biophys Acta 1997 Sep. 12; 1353 (3): 307-317), but is not limited thereto.

The vitamin $D_3$ responsive sequences of human and other species with one or more nucleotide substitutions, deletions, additions, and/or insertions, can be included in this invention as long as they have an activity to cause a positive vitamin $D_3$ responsee to a heterologous or homologous promoter. In fact, this invention demonstrated that vitamin $D_3$ responsive sequences with mutations in the Sp1-2 region retain a high activity as such mentioned above (Example 4, FIG. 8). In contrast, the introduction of mutations to the Sp1-1 sequence or CCAAT box is not preferred because it is likely that the activity will be eliminated.

The vitamin $D_3$ responsive sequences described in this invention are preferably used in the screening for compounds that regulate the expression of the p27$^{Kip1}$ gene. Therefore, this invention provides screening methods using the vitamin $D_3$ responsive sequences to identify compounds that regulate the expression of the p27$^{Kip1}$ gene. Compared to screening methods using the long 5' promoter region of the p27$^{Kip1}$ gene, screening methods using the vitamin $D_3$ responsive sequences of this invention are useful, for example, for screening compounds (including vitamin $D_3$ derivatives) that specifically interact with NF-Y or Sp1. Thus, the screening methods of the instant invention have an enormous advantage when it comes to developing novel pharmaceutical agents with fewer side effects.

One embodiment of the screening methods of the present invention involves using a reporter construct comprising vitamin $D_3$ responsive sequences of the present invention. In more detail, the method comprises the following steps:

(a) contacting a test sample with a cell into which a vector has been introduced in frame, wherein said vector contains a reporter gene operably linked behind vitamin $D_3$ responsive sequences;

(b) detecting reporter activity in said cell; and (c) selecting a compound that increases or decreases reporter activity, compared to the activity in the absence of the test sample (control).

The first step in the screening method of this invention is to construct a vector comprising a reporter gene operably linked behind vitamin $D_3$ responsive sequences. Herein, "operably linked" means that the reporter gene is connected downstream of vitamin $D_3$ responsive sequences in frame, so that the reporter gene is expressed when the vitamin $D_3$ responsive sequences are activated. The p27$^{Kip1}$ promoter region, which includes the vitamin $D_3$ responsive sequences of the present invention, can be used to ensure the expression of such a reporter gene. Alternatively, a heterologous promoter may be inserted between the vitamin $D_3$ responsive sequences of the instant invention and the reporter gene. Here, the heterologous promoter is not limited as long as it does not have vitamin $D_3$ responsiveness per se and as long as it has vitamin $D_3$ responsiveness under the regulation of the vitamin $D_3$ responsive sequences of the present invention. For example, minimum promoters like the SV40 early promoter and the TK promoter, can be preferably used. The distance required for NF-Y and Sp1, which bind to the vitamin $D_3$ responsive sequences, to interact with general transcription factors varies depending on the factors. Therefore, when the vitamin $D_3$ responsive sequences are used with a heterologous promoter, tandem copies of the sequences can be used if necessary. Usually, 3 to 5 tandem copies of the vitamin $D_3$ responsive sequences of the present invention are constructed and the construct with the highest activity can be used as vector.

Any reporter gene can be used for the screening methods of the present invention as long as its expression can be detected. Examples include the firefly luciferase gene, secreted alkaline phosphatase gene, and chloramphenicol acetyl transferase (CAT) gene.

The constructed vectors are then introduced into cells, and the resulting cells are contacted with a test sample. Any cell can be used for the introduction as long as it responds to vitamin $D_3$ stimulation and expresses the reporter gene within the introduced vector. To screen for candidates of pharmaceutical agents, mammalian cells, including human cells, are preferably used. For example, U937 cells are preferably used. Yeast and *E. coli* can be used depending on the experiment. However, none of these examples are to be construed as limiting.

Vectors are introduced into cells using known methods, such as, electroporation, calcium phosphate, DEAE-dextran, cationic liposome, or lipofection methods.

In the screening methods of this invention, reporter activity is detected using cells prepared as above after contacting the cells with test samples. Any sample, including cell extracts, cell culture supernatants, microbial fermentation products, marine organism extracts, plant extracts, purified or crude proteins, peptides, nonpeptidic compounds, synthetic low molecular weight compounds, and natural products, can be tested. When compounds that suppress the expression of the p27$^{Kip1}$ gene are screened (in addition to the test sample) vitamin $D_3$ can be contacted with the subject cell. Depending on the reporter gene used, the reporter activity can be detected by a method known to those skilled in the art.

Compounds that are capable of enhancing p27$^{Kip1}$ gene expression can be screened by selecting those that increase reporter activity, compared to the reporter activity in cells in the absence of the test sample (control). It is also possible to identify inhibitors that suppress the p27$^{Kip1}$ gene expression by selecting those that decrease reporter activity, compared to the control.

This invention also demonstrates (by gel shift assay) that NF-Y protein binds to the CCAAT box, a vitamin $D_3$ responsive sequence of the present invention. It also demonstrates that Sp1 protein binds to the Sp1-1 sequence, the other vitamin $D_3$ responsive sequence of the present invention (Examples 2 and 5). Moreover, it was revealed that both Sp1 and NF-Y proteins are required for vitamin $D_3$-induced p27$^{Kip1}$ transcription (Example 3). Based on the above observations, the present inventors developed methods of screening for compounds that regulate the expression of the p27$^{Kip1}$ gene using as indexes the binding of NF-Y protein with the CCAAT box, and Sp1 protein with the Sp1 sequence (Sp1-1 sequence), the vitamin $D_3$ responsive sequences of the present invention.

Other embodiments of the method of screening for a compound that regulates the expression of the p27$^{Kip1}$ gene comprises the steps of:

(a) contacting NF-Y protein with a DNA comprising (i) a DNA comprising the CCAAT box in the 5' regulatory region of human p27$^{Kip1}$ gene, or (ii) a non-human-derived DNA corresponding to the DNA of (i), in the presence of a test sample;

(b) detecting binding of NF-Y protein with said DNA; and (c) selecting a compound that increases or decreases the binding activity of said DNA with the NF-Y protein when compared to the activity in the absence of the test sample; and also, a method comprises the steps of:

(a) contacting the Sp1 protein with a DNA comprising (i) a DNA comprising the Sp1 sequence in the 5' regulatory region of human p27$^{Kip1}$ gene, or (ii) a non-human-derived DNA corresponding to the DNA region of (i), in the presence of a test sample;

(b) detecting binding of Sp1 protein with said DNA; and (c) selecting a compound having an activity to increase or decrease the binding activity of the DNA with the Sp1 protein when compared to the activity in the absence of the test sample.

Specifically, labeled Sp1 or CCAAT boxes are bound to assay plates and recombinant Sp1 or NF-Y proteins are added to the plates in the presence of a test sample. The binding of the two is detected via standard techniques like antibodies, etc. The binding activity is compared with the binding activity in the absence of the sample (control) and compounds that change the binding activity are selected. The assay plates can also be bound to recombinant proteins and then treated with DNA probes in the presence of test samples.

The one-hybrid system can also be used to screen for compounds. Specifically, a vector that contains the Sp1 sequence and a reporter gene operably linked to the sequence, and a Sp1 expression vector are introduced into animal cells, yeast, or *E. coli*. A vector that contains the CCAAT box and a reporter gene operably linked to the sequence and NF-Y expression vector can also be used. The reporter activities in the cells are assayed in the presence of the test samples. The activity is compared to the activity detected without the test samples. Then compounds that enhance or reduce the reporter activity are selected.

Compounds isolated by the screening methods of the present invention can be applied to therapy. The p27$^{Kip1}$ protein is known to stop cell proliferation by inhibiting cyclin/cdk. Therefore, compounds that enhance p27$^{Kip1}$ gene expression can be useful for treating cell proliferation-related diseases, such as, malignant tumors, atherosclerosis, or restenosis caused by vascular endothelial cell proliferation occurring after balloon coronary distention surgery. On the other hand, compounds that suppress p27$^{Kip1}$ gene expression can be effective for treatments that require cell proliferation, such as, aplastic anemia, liver cirrhosis, and wound healing.

It was reported that the mRNA production from p27$^{Kip1}$ is induced by vitamin $D_3$ in U937 cells (Liu, M. et al. (1996) Genes Dev., 10, 142-153). However, it was the present inventors who actually showed that vitamin $D_3$ acts as a positive regulator by developing screening systems that use the above reporter construct and screening systems that detect the binding of NF-Y protein and Sp1 protein to the CCAAT box and Sp1 sequence (Sp1-1 sequence), respectively (Examples 3-6). These findings indicate that the screening systems of the present invention are useful in screening for compounds that regulate p27$^{Kip1}$ gene expression.

The inventors demonstrated that vitamin $D_3$ enhances the binding of NF-Y protein to the CCAAT box and also the binding of Sp1 protein to the Sp1 sequence (Sp1-1 sequence) located in the vitamin $D_3$-responsive sequences 5' upstream of p27$^{Kip1}$ gene. These findings indicate that vitamin $D_3$ and derivatives thereof can be used as enhancers of the binding activities. Therefore, this invention provides pharmaceutical agents that contain vitamin $D_3$ or derivatives thereof as active ingredients that enhance binding of NF-Y protein to the CCAAT box located in the 5' regulatory region of the p27$^{Kip1}$ gene. Also provided are pharmaceutical agents that contain vitamin $D_3$, or derivatives thereof, as effective ingredients that enhance the binding of the Sp1 protein to the Sp1 sequence located in the 5' regulatory region of the p27$^{Kip1}$ gene.

The term "pharmaceutical agent" as used herein includes both reagents and medicines.

The "vitamin $D_3$ derivatives", effective ingredients of the pharmaceutical agents of the present invention, means compounds with a general structural formula as indicated below:

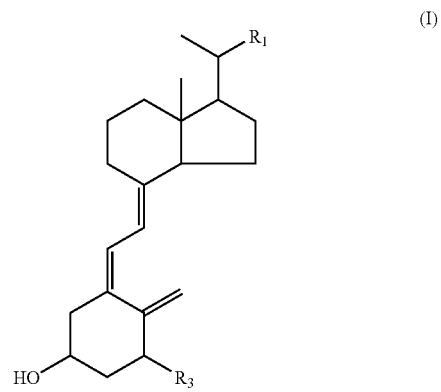

(I)

wherein, R1 indicates —O—$R_2$, —S—$R_2$, —$CH_2$—$R_2$, or —CH=$R_2$;

$R_2$ indicates a linear hydrocarbon group with 1 to 10 carbons which may be substituted by one or more hydroxyl groups; and $R_3$ indicates either hydrogen or hydroxyl group.

These vitamin $D_3$ derivatives are disclosed in Examined Published Japanese Patent Application No. (JP-B) Hei 3-74656, International Patent Publication WO 94/14766, International Patent Publication WO 95/27697, Published Japanese Translation of International Publication No. Hei 4-506965, Published Japanese Translation of International Publication No. Hei 4-503669, and Unexamined Published Japanese Patent Application No. (JP-A) Sho.

In structure (I), the linear hydrocarbon group with 1 to 10 carbons that can be substituted with hydroxyl groups, is either straight or branched and can contain one or more unsaturated bonds, such as, double or triple bonds, preferably double bonds. Groups that contain no unsaturated bonds or one double bond are preferable for the linear hydrocarbon group with 1 to 10 carbons.

Linear hydrocarbon groups, such as, those disclosed above with no unsaturated bonds include, methyl, ethyl, n-propyl, i-propyl, n-butyl, i-butyl, s-butyl, t-butyl, pentyl, hexyl, heptyl, octyl, nonyl, and decanyl groups. Preferably they include, 3-methylbutyl, 3-ethylpentyl, 4-methylpentyl, 3-(n-propyl)hexyl, 4-ethylhexyl, 5-methyhexyl, 6-methyheptyl, 5-ethylheptyl, 4-(n-propyl)heptyl groups, and more preferably, 3-methylbutyl, 3-ethylpentyl, 4-methylpentyl, and 4-ethylhexyl groups and most preferably, they include the 3-methylbutyl group.

The linear hydrocarbon groups may or may not be substituted with a hydroxyl group. The number of hydroxyl groups used for substitution is, for example, one, two, or three, (preferably one or two, and more preferably one).

Alkyl groups with carbons 1 to 10, which have more than one hydroxyl group substitution, include 3-hydroxy-3-methylbutyl, 2-hydroxy-3-methylbutyl, 4-hydroxy-3-methylbutyl, 2,3-dihydroxy-3-methylbutyl, 2,4-dihydroxy-3-methylbutyl, 3,4-dihydroxy-3-methylbutyl, 3-hydroxy-3-ethylpentyl, 2-hydroxy-3-ethylpentyl, 4-hydroxy-3-ethylpentyl, 2,3-dihydroxy-3-ethylpentyl, 2,4-dihydroxy-3-ethylpentyl, 3,4-dihydroxy-3-ethylpentyl, 4-hydroxy-4-methylpentyl, 3-hydroxy-4-methylpentyl, 5-hydroxy-4-methylpentyl, 3,4-dihydroxy-4-methylpentyl, 3,5-dihydroxy-4-methylpentyl, 4,5-dihydroxy-4-methylpentyl, 3-hydroxy-3-(n-propyl)hexyl, 4-hydroxy-3-(n-propyl)hexyl, 2-hydroxy-3-(n-propyl)hexyl, 2,3-dihydroxy-3-(n-propyl)hexyl, 3,4-dihydroxy-3-(n-propyl)hexyl, 2,4-dihydroxy-3-(n-propyl)hexyl, 3-hydroxy-4-ethylhexyl, 4-hydroxy-4-ethylhexyl, 5-hydroxy-4-ethylhexyl, 3,4-dihydroxy-4-ethylhexyl, 3,5-dihydroxy-4-ethylhexyl, 4,5-dihydroxy-4-ethylhexyl, 4-hydroxy-5-methylhexyl, 5-hydroxy-5-methylhexyl, 6-hydroxy-5-methylhexyl, 4,5-dihydroxy-5-methylhexyl, 4,6-dihydroxy-5-methylhexyl, 5,6-dihydroxy-5-methyhexyl, 5-hydroxy-6-methylheptyl, 6-hydroxy-6-methylheptyl, 7-hydroxy-6-methylheptyl, 5,6-dihydroxy-6-methylheptyl, 5,7-dihydroxy-6-methyheptyl, 6,7-dihydroxy-6-methylheptyl, 4-hydroxy-5-ethylheptyl, 5-hydroxy-5-ethylheptyl, 6-hydroxy-5-ethylheptyl, 4,5-dihydroxy-5-ethylheptyl, 4,6-dihydroxy-5-ethylheptyl, 5,6-dihydroxy-5-ethylheptyl, 3-hydroxy-4-(n-propyl)heptyl, 4-hydroxy-4-(n-propyl)heptyl, 5-hydroxy-4-(n-propyl)heptyl, 3,4-dihydroxy-4-(n-propyl)heptyl, 3,5-dihydroxy-4-(n-propyl)heptyl, and 4,5-dihydroxy-4-(n-propyl)heptyl groups. Preferably, 3-hydroxy-3-methylbutyl, 2-hydroxy-3-methylbutyl, 2,3-dihydroxy-3-methylbutyl, 3,4-dihydroxy-3-methylbutyl, 3-hydroxy-3-ethylpentyl, 2,3-dihydroxy-3-ethylpentyl, 3,4-dihydroxy-3-ethylpentyl, 4-hydroxy-4-methylpentyl, 3,4-dihydroxy-4-methylpentyl, 4,5-dihydroxy-4-methylpentyl, and 4-hydroxy-4-ethylhexyl groups are included. More preferably, 3-hydroxy-3-methylbutyl, 3-hydroxy-3-ethylpentyl, and 4-hydroxy-4-methylpentyl groups, and most preferably, 3-hydroxy-3-methylbutyl group.

Examples of linear hydrocarbon groups with unsaturated bonds include the saturated hydrocarbon groups described above containing single or multiple bonds that are unsaturated, preferably double bonds. The particularly preferred hydrocarbon group containing unsaturated bonds is, for example, $=CH-CH=CH-CH(CH_2CH_3)_2$, while the hydrocarbon group substituted with a hydroxyl group is $=CH-CH=CH-C(CH_2CH_3)_2OH$. In structure (I), R3 is preferably a hydroxyl group.

When compounds (including vitamin $D_3$) isolated by the screening methods of the present invention for their activity to regulate $p27^{Kip1}$ gene expression are used as pharmaceutical agents for humans or other mammals (such as mice, rats, guinea pigs, rabbits, chickens, cats, dogs, sheep, pigs, cows, monkeys, baboons, and chimpanzees) the purified compounds or proteins can be formulated according to well known pharmaceutical methods and administered, or they can be directly administered into the subjects.

For example, the pharmaceutical agents can be given orally as pills (if necessary as sugar-coated pills) capsules, elixirs, and microcapsules. Alternatively, they can be administrated non-orally as injections of sterile solutions or suspensions with water or other pharmaceutically acceptable solutions. For example, the compounds or proteins can be formulated with pharmaceutical acceptable carriers or media, specifically sterile water, physiologic saline, plant oils, emulsifiers, suspension, detergents, stabilizers, flavoring agents, excipients, vehicles, preservatives, or binders, at unit dosage forms required for generally accepted formulation of pharmaceutical agents. The amount of effective ingredient present in these pharmaceutical agents makes it possible to acquire a suitable amount within the prescribed range.

Additives that can be used for formulating pills and capsules include binders, such as gelatin, corn starch, tragacanth gum, and arabic gum, excipients such as crystalline cellulose, swelling agents such as corn starch, gelatin, and alginic acid, lubricants such as magnesium stearate, sweeteners such as sucrose, lactose, and saccharine, and flavoring agents such as peppermint, akamono oil (oil of a plant generally known in the west as "Celebes Goby"; scientific name: "*Glossogobius celebius*"). When formulating capsules, a liquid carrier such as oil can be added to the above. Sterile compositions for injections can be formulated with vehicles such as distilled water according to standard methods for formulating pharmaceutical agents.

Solutions used for injections can be physiological saline, and isotonic solutions containing glucose or other adjuvants, such as, D-sorbitol, D-mannose, D-mannitol, and sodium chloride. Suitable solubilizers, such as, alcohol, (specifically ethanol), polyalcohol, propylene glycol, polyethylene glycol, and non ionic detergents such as polysorbate 80 (TM) or HCO-50 can may also be used.

Sesame oil and soybean oil and such can be used as oleaginous solutions for injections. These can be used together with solubilizers, such as, benzyl benzoate and benzyl alcohol. Oleaginous solutions can also be used with buffering agents, such as, phosphate buffer and sodium acetate buffer, painkillers such as procaine hydrochloride, stabilizing agents such as benzyl alcohol and phenol, and anti-oxidation agents. The formulated solution to be used for injections can be kept in suitable ampules.

The pharmaceutical agent can be administrated via standard methods to patients by intraarterial, intravenous, or subcutaneous injections, or given intra-nasally, transbronchially, intramuscularly, percutaneously, or orally. The dosage of the pharmaceutical agent varies according to the patient's body weight and age, and the administration method. A proper dosage can be selected by those in the art. If the compounds can be encoded by DNAs, the DNAs are used for gene therapy by inserting the DNAs into suitable vectors. Drug dosage varies according to the patient's body weight, age, symptoms, and administration method.

The dosage of the pharmaceutical agents of this invention would vary depending on the symptoms; however, in the case of an oral administration for an adult (weighing 60 kg), it is 0.1 mg to 100 mg, preferably 1.0 mg to 50 mg, and more preferably 1.0 mg to 20 mg per day.

When pharmaceutical agents are administered non-orally, the unit dosage varies depending on the symptoms, the administration method, the patient, and organs to which the pharmaceutical agents are administered. For example, in the case of injections, an adult (weighing 60 Kg) is generally injected intravenously with 0.01 mg to 30 mg, preferably 0.1 mg to 20 mg, and more preferably 0.1 mg to 10 mg of the pharmaceutical agent per day. For other animals, the dosage of the pharmaceutical agent is calculated based on the dose converted to body surface area or dose per 60 Kg body weight).

BEST MODE FOR CARRYING OUT THE INVENTION

Figure 1:
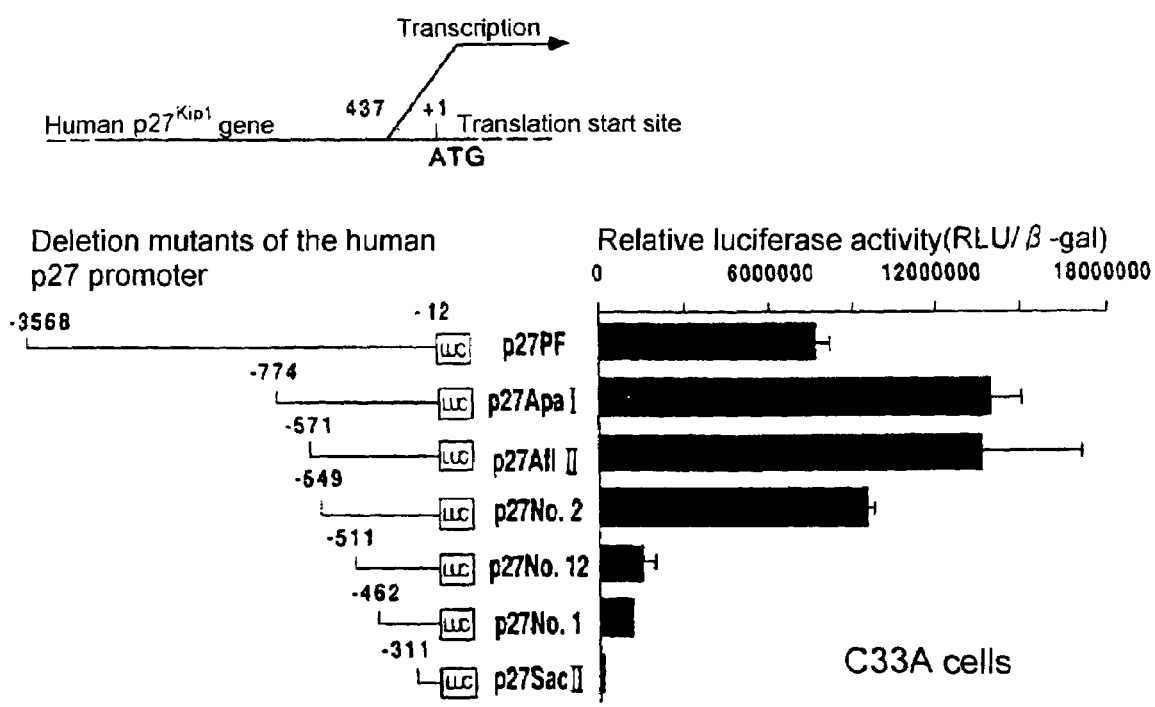
FIG. 1 shows the effect of 5' deletion mutations on the promoter activity of the human p27$^{Kip1}$ gene in C33A cells. First, the luciferase reporter gene was linked to various 5'-deletion mutants of p27$^{Kip1}$ promoter. 2 µg of each plasmid was transiently transfected into C33A cells with 1 µg of pACT β-gal and luciferase activities were analyzed after 48 hrs. The luciferase activities in the cell extracts were determined according to the method described in this invention. The diagrams of each construct are shown at left. Data shown are means (bars indicate standard deviation) (n=3).

The present invention is specifically illustrated below with reference to Examples, but it is not to be construed as being limited thereto.

Human cervical cancer cell line, C33A, human osteosarcoma cell lines, U2OS and MG63 were maintained in Dulbecco modified Eagle media containing 10% (v/v) fetal bovine serum (FBS) and cultivated in an atmosphere of 5% $CO_2$ at 37° C. Human myelomonocytic cell line U937 (a generous gift from Dr. Y. Honma of the Saitama Cancer Research Institute, Saitama, Japan) was cultivated in Roswell Park Memorial Institute (RPMI) 1640 media supplemented with 10% (v/v) fatal bovine serum in an atmosphere of 5% $CO_2$. The induction of monocytic differentiation was performed by cultivation of the cells in the presence of 1,25-dihydroxy vitamin $D_3$ (Wako, Tokyo, Japan).

The construction of the plasmids and mutagenesis was conducted as follows. The human $p27^{Kip1}$-luciferase fusion plasmid, p27PF, and deletion mutants thereof, p27ApaI, p27AfiII, and p27SacII are already known (Minami, S. et al. (1997) FEBS Lett., 411, 1-6). The other deletion mutants, p27No.1, p27No.2, p27.12, and p27MB-435 were constructed by Mungbean-Exonulease III system using Kilosequence Deletion Kit (Takara). The deletion fragments were subcloned into pGL2 Basic vector (Promega) at XhoI site.

p27PF plasmids with point mutations (p27mSp1-1, p27mSp1-2, and p27mCTF) were constructed via site-directed mutagenesis (Landt, O. et al. (1990) Gene, 96, 125-128) using Quick Change Site-Directed Mutagenesis Kit (Stratagene). One strand of the oligonucleotides used is as follows. Underlines show where mutations were introduced.

P27mSp1-1: 5'-CAGCCTCGGCGGG ATGGCTCCCGCCG-3' (SEQ ID NO: 2);

P27mSp1-2: 5'-CGGGGCGGCTCC TACCGCCGCAACCAATG-3' (SEQ ID NO: 3); and

P27CTF: 5'-GCCGCCGCAACCTTTGGATCTCCTCC-3' (SEQ ID NO: 4).

Each ApaI-RindIII fragment, corresponding to positions −774/−12 of the three mutants was subcloned again into ApaI-HindIII digested p27PF to prevent the occurrence of undesirable mutations. All constructs prepared were subjected to restriction enzyme analysis and sequencing.

Furthermore, the present inventors generated constructs containing four tandem copies of the specific sequence of the $p27^{Kip1}$ promoter fused to a minimal promoter. A double-stranded 52-bp DNA fragment containing a 44-bp sequence corresponding to the −555/−512 region of the human $p27^{Kip1}$ promoter and linker sites (indicated by lower case letters below) at both ends was generated from two oligonucleotides. The top strand (5'-agggAGCCTCGGCGGGGCG-GCTCCCGCCGCCGCAACCAATGGATCTCC-3') (SEQ ID NO: 5) and the bottom strand (5'-ccctGGAGATCCATTG-GTTGCGGCGGCGGGAGCCGCCCCGCCGAGGCT-3') (SEQ ID NO: 6) were annealed, ligated, blunted and subcloned into the SmaI site upstream of the SV40 early promoter in the PicaGene Promoter Vector 2 (Nippon Gene, Tokyo, Japan) in a forward or reverse orientation to generate PGPV2[−555/−512wild]$_4$ and PGPV2[R−555/−512wild]$_4$, respectively. Similarly, three types of double-stranded mutated oligonucleotides of the 44-bp sequence were also inserted into the same vector to generate the mutated constructs, PGPV2[−555/−512mSp1-1]$_4$, PGPV2[−555/−512 mSp1-2]$_4$, PGPV2[−555/−512mCTf]$_4$ (see Table 1). Oligonucleotides used in Example 3-6 are shown as follows (SEQ ID NOS: 5, 6, and 18-31).

TABLE 1

| Oligomer | Sequence | (SEQ ID NO:) | Reference |
|---|---|---|---|
| −555/−512wild | 5'-agggAGCCTCGGCGGGGCGGCTCCCGCCGCCGCAACCAATGGATCTCC-3' | (5) | Example |
| | 3'-TCGGAGCCGCCCCGCCGAGGGCGGCGGCGTTGGTTACCTAGAGGtccc-5' | (6) | |
| |                Sp1±1   Sp1±2     CTF | | |
| −555/−512mSp1-1 | 5'-agggAGCCTCGGCGGG<u>AT</u>GGCTCCCGCCGCCGCAACCAATGGATCTCC-3' | (18) | Example |
| | 3'-TCGGAGCCGCCC<u>TA</u>CCGAGGGCGGCGGCGTTGGTTACCTAGAGGtccc-5' | (19) | |
| −555/−512mSp1-2 | 5'-agggAGCCTCGGCGGGGCGGCTCC<u>TA</u>CCGCCGCAACCAATGGATCTCC-3' | (20) | Example |
| | 3'-TCGGAGCCGCCCCGCCGAGG<u>AT</u>GGCGGCGTTGGTTACCTAGAGGtccc-5' | (21) | |
| −555/−512mCTF | 5'-agggAGCCTCGGCGGGGCGGCTCCCGCCGCCGCAACC<u>TTT</u>GGATCTCC-3' | (22) | Example |
| | 3'-TCGGAGCCGCCCCGCCGAGGGCGGCGGCGTTGG<u>AAA</u>CCTAGAGGtccc-5' | (23) | |
| −534/−512wild | 5'-CGCCGCAACCAATGGATCTCC-'3 | (24) | Example |
| | 3'-GCGGCGTTGGTTACCTAGAGG-5' | (32) | |
| −534/−512mCTF | 5'-CGCCGCAACC<u>TTT</u>GGATCTCC-3' | (25) | Example |
| | 3'-GCGGCGTTGG<u>AAA</u>CCTAGAGG-5' | (33) | |
| Sp1wild | 5'-ATTCGATCGGGGCGGGGCGAGC-3' | (26) | Literature 1 |
| | 3'-TAAGCTAGCCCCGCCCCGCTCC-5' | (34) | |
| Sp1mt | 5'-ATTCGATCGGG<u>AT</u>GGGGCGAGC-3' | (27) | Literature 1 |
| | 3'-TAAGCTAGCCC<u>TA</u>CCCCGCTCC-5' | (35) | |
| NF-Ywild | 5'-ACTTTTAACCAATCAGAAAAAT-3' | (28) | Literature 2 |
| | 3'-TGAAAATTGGTTAGTCTTTTTA-5' | (36) | |
| C/EBP-αwild | 5'-CTAGTACCTTATTTGAACTAACCAATCAGTTCG-3' | (29) | Literature 2 |
| | 3'-GATCATGGAATAAACTTGATTGGTTAGTCAAGC-5' | (37) | |
| NF-Iwild | 5'-TTTTGGATTGAAGCCAATATGATAA-3' | (30) | Literature 3 |
| | 3'-AAAACCTAACTTCGGTTATACTATT-5' | (38) | |
| NF-Imt | 5'-TTTTGGATTGAAGC<u>TTT</u>ATGATAA-3' | (31) | Literature 3 |
| | 3'-AAAACCTAACTTCGG<u>AAA</u>TACTATT-5' | (39) | |

In the above table, the Sp1 and NF-Y consensus sequences are indicated by thick letters. The mutated sequences are highlighted by underlines. The linker sequences at the end of the oligomers are indicated by lower case letters.

EXAMPLE 1

Identification of Cis Arrangement for p27$^{Kip1}$ Promoter

Mutants containing stepwise deletions between −774 and −435 were constructed as above in order to identify the cis arrangement necessary for human p27$^{Kip1}$ promoter activity. Each construct was transiently transfected into C33A, MG63, and U2OS cells. C33A was used as a cell line that had mutations in both the p53 and RB genes. U2OS was used as a cell line that had no mutations in either gene. MG63 was used as a cell line that had a rearrangement in p53, and RB cell as an intact cell.

C33A cells (3×10$^5$ cells), MG63 cells (3×10$^5$ cells), and U2OS cells (3×10$^5$ cells) were plated on tissue culture plates (6 cm in diameter). Each cell was co-transfected after 24 hrs with 2 μg of reporter plasmids and 1 μg of pACT β-gal plasmid including β-galactosidase gene that is expressed by the actin promoter using the calcium phosphate co-precipitation method (Sambrook, J. et al. (1989) Molecular Cloning: A Laboratory Manual, 2nd Edn., Cold Spring Harbor Laboratory Press, Cold Spring Harbor, N.Y.). Cells were harvested as described previously (Brasier, A. R. et al. (1989) Biotechniques, 7, 1116-1122) at 24 hrs and 48 hrs after transfection and cell extracts were prepared for luciferase assay. Luciferase activities in each cell extract sample were measured and normalized by β-galactosidase activity in each cell extract. All transfection assays were done in triplicate and each experiment was repeated at least twice.

FIG. 1 shows that deletions up to −549 (p27No.2) in the C33A cells did not result in a significant change in promoter activity. However, deletions up to −511 (p27No.12) in C33A cells caused a significant decrease. U2OS and MG63 cells showed similar results (data not shown). These results indicate that the region downstream from −549 contains the regulatory sequences. In particular, it was found that deletions up to −549 and −511 cause a significant decrease in promoter activity. This indicates that the region between −549 and −511 (−112 to −74 relative to the transcription initiation site) contains the sequence necessary for basal promoter activity.

Figure 2:
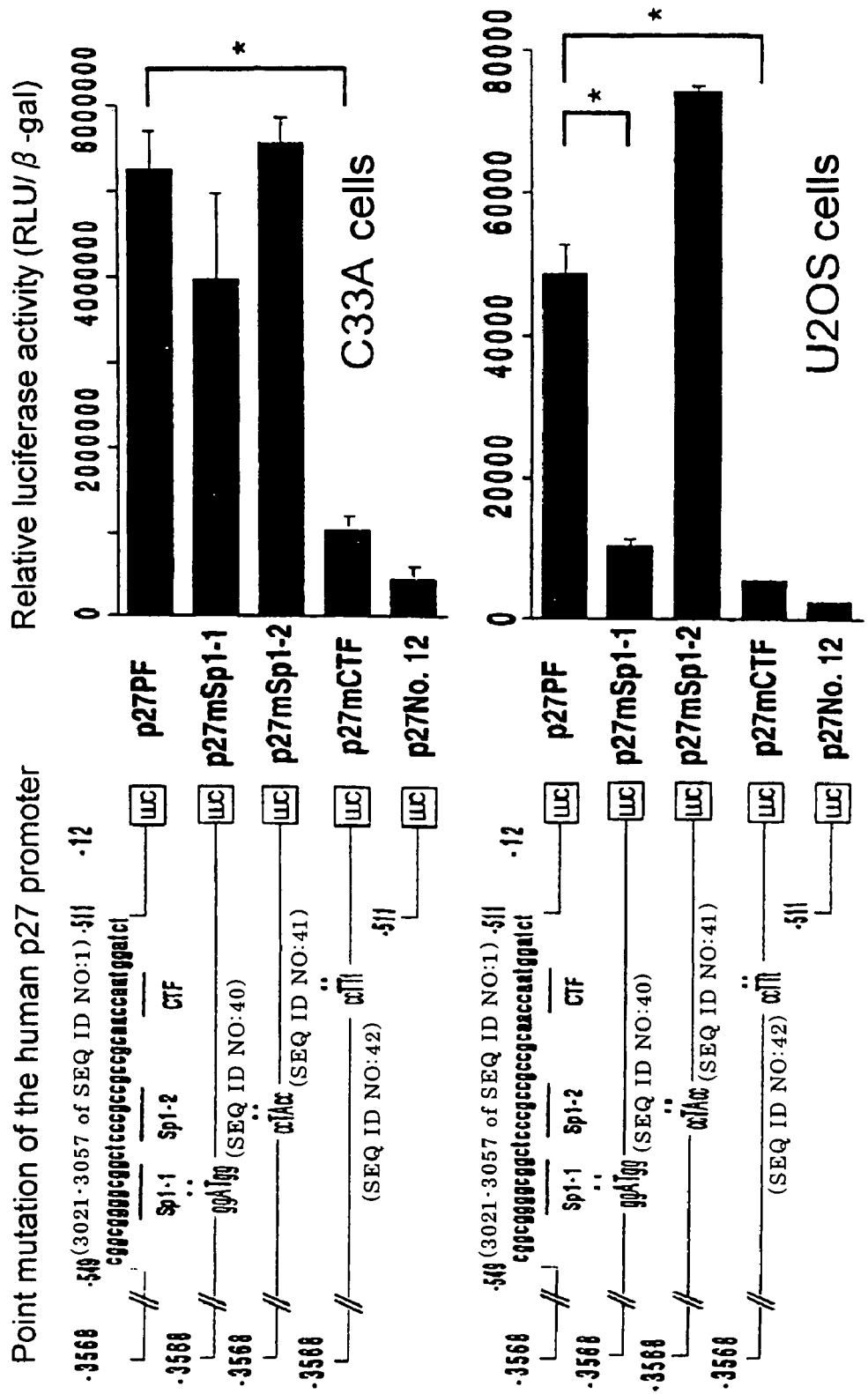
FIG. 2 shows the results of mutation analysis used to identify the cis arrangement required for p27$^{Kip1}$ basal promoter activity in C33A and U2OS cells. Three mutants (SEQ ID NOS:40-42) showed on the left have the same sequence as wild type p27PF (nucleotides 3021-3057 of SEQ ID NO:1) except the regions where the nucleotides are written in capital. 2 µg of each plasmid was transiently transfected into C33A or U2OS cells with 1 µg of pACTβ-gal, and luciferase activities were analyzed after 48 hrs. Data shown are means (bar indicates standard deviation) (n=3). *, P<0.005.

This 39 base region contains two consensus Sp1 binding sites and one CCAAT box (CTF region). The inventors named the two Sp1 binding sequences as Sp1-1 and Sp1-2 (FIG. 2). Mutations were introduced into Sp1-1 (p27mSp1-1), Sp1-2 (p27mSp1-2), or the CCAAT box (p27CTF) in the p27PF plasmid which contains the entire promoter region in order to examine the involvement of Sp1-1, Sp1-2, and the CCAAT box in p27$^{Kip1}$ transcriptional regulation (FIG. 2). These constructs were transiently transfected into C33A, MG63, and U2OS cells as described previously to determinate the luciferase activity for each. As shown in FIG. 2, 2 bp mutation in the CCAAT box significantly decreased p27PF promoter activity in all cell lines. A mutation in the Sp1-2 site did not affect promoter activity, but a mutation in Sp1-1 site significantly decreased p27PF promoter activity in the U2OS cell line (FIG. 2 lower panel). A mutation in Sp1-1 site did not decrease promoter activity in C33A and MG63 cell lines to the same extent as in the U2OS cell line (FIG. 2; data in MG63 not shown). This result indicates that the CCAAT box is necessary for maximizing basal promoter activity of p27$^{Kip1}$ gene and that the Sp1-1 site is required for cell dependent promoter activation.

EXAMPLE 2

Identification of Factors that Interact with p27$^{Kip1}$ Promoter in Trans

An oligonucleotide spanning −530 to −510 of the human p27$^{Kip1}$ promoter that includes the CCAAT box was labeled with $^{32}$P and EMSA (gel shift assay) was conducted to identify factor(s) that interact with the CCAAT box in trans.

Nuclear extracts were prepared according to the method described by Andrews and Faller (Andrews, N. C. and Faller, D. V. (1991) Nucleic Acids Res., 19, 2499). The reaction solution (20 μl final) for Gel Shift Assay contained 20 mM Tris-HCl (pH 8.0), 50 mM NaCl, 1 mM DTT, 1 mM EDTA, 10% glycerol, 0.05% Nonidet P-40, 5 μg Bovine serum albumin (BSA), 2 μg poly(dI-dC), and 5 μg nuclear extract. The mixture was pre-incubated at room temperature for 5 minutes and then probe DNA (about 2 ng, 20,000 cpm) was added to the mixture. The binding reaction was allowed to proceed for 20 minutes at room temperature. The product was then subjected to electrophoresis on a non-denaturing gel containing 5% polyacrylamide-bisacrylamide (29:1), 0.5×TBE for 120 minutes at 10 V/cm. The sequence of one strand of oligonucleotides used for the assays (including the oligonucleotides that specifically bind to transcription factors used in the experiments below) are shown with underlines in places where mutations were introduced:

WT−530/−510, 5'-CTAGCGCCGCAACCAATGGATCTCC-3' (SEQ ID NO: 7);

MUT−530/−510, 5'-CTAGCGCCGCAACCTTTGGATCTCC-3' (SEQ ID NO: 8);

NF-I, 5'-CTAGTTTTGGATTGAAGCCAATATGATAA-3' (SEQ ID NO: 9) (Jones, K. A. et al. (1987) Cell, 48, 79-89);

NF-Y, 5'-ACTTTTAACCAATCAGAAAAATCTAG-3' (SEQ ID NO: 10) (Dorn, A. et al. (1987) Cell, 50, 863-872); and CP2, 5'-CTAGTGACCAGTTCCAGCCACTCTTTA-3' (SEQ ID NO: 11) (Chodosh, L. A. et al. (1988) Cell, 53, 11-24).

Competition analysis was performed by mixing the indicated amount of appropriate competitor DNAs to the binding reactions prior to addition of nuclear extracts. In supershift experiments described later, antibodies against NF-YB (IgG fraction) or C/EBPα (sc-7204X; Santa Cruz) were added to the incubation mixtures containing nuclear proteins before addition of probe DNAs. Antibody against NF-YB was a gift from Dr. R. Mantovani.

Three shifted bands were observed when nuclear extracts from C33A were incubated with the probe. The slowest migrating complex was competed out by an excess of unlabeled oligonucleotide WT−530/−510, but not competed out by an excess of MUT−530/−510 where CCTTT was mutated to CCAAT. This result indicates that nuclear protein(s) can bind specifically to the CCAAT box of the WT−530/−510 probe.

Figure 3:
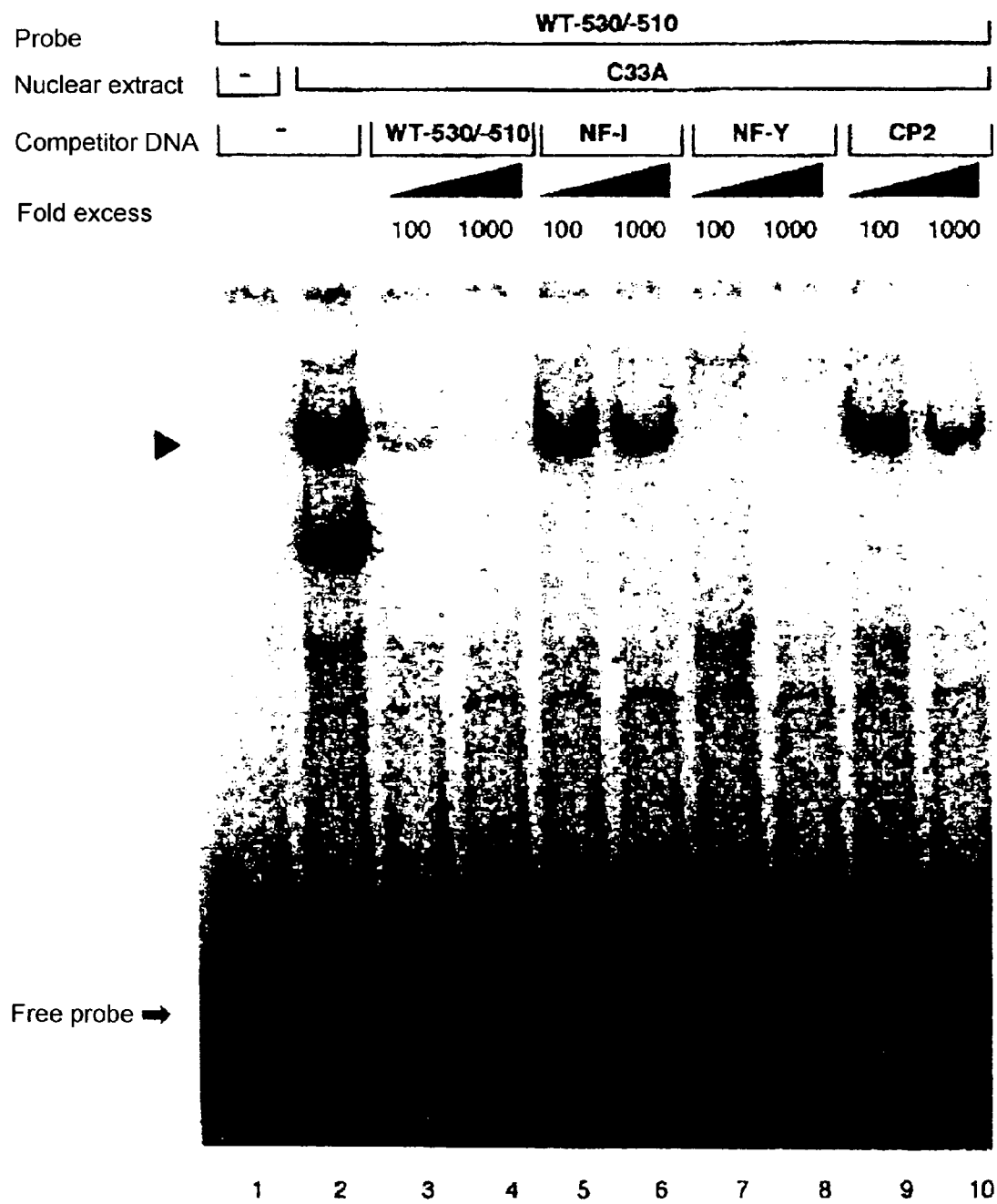
FIG. 3 shows a photograph indicating binding and competition analysis of the CCAAT box located in the p27$^{Kip1}$ gene with nuclear proteins from C33A cells. Electrophoresis migration shift assay (EMSA) (gel shift assay) was carried out under the presence of nuclear extracts prepared from C33A cells. A set of oligonucleotides containing the CCAAT box between −530 and −510 (WT-530/−510) was used as a probe. Nuclear extracts were incubated with $^{32}$P-labeled WT-530/−510 in the absence of (−) (lane 1 and 2) or in the presence of ×100 or ×1000 fold amount of various unlabeled oligonucleotides that were able to bind to each CCAAT binding protein. Specific bands with decreased mobility (retarded bands), including CCAAT box binding protein(s), are indicated on the left.

The CCAAT box is known to interact with various nuclear proteins including NF-Y (CP1), NF-I (CTF), CP2, and C/EBP (Dorn, A. et al. (1987) Cell, 50, 863-872; Chodosh, L. A. et al. (1988) Cell, 53, 11-24; Hooft van Huijsduijnen, R. A. et al. (1987) Nucleic Acids Res., 15, 7265-7282; Maity, S, N. et al. (1990) Proc. Natl. Acad. Sci. USA, 87, 5378-5382; Mahoney, C. W. et al. (1992) J. Biol. Chem., 267, 19396-19403). To identify which nuclear proteins bind to the −524/−519 CCAAT box, competitive EMSA (competitive gel shift assay) was conducted using a CCAAT box having an oligonucleotide known to bind to some of the transcription factors (Jones, K. A. et al. (1987) Cell, 48, 79-89; Dorn, A. et al. (1987) Cell, 50, 863-872; Chodosh, L. A. et al. (1988) Cell, 53, 11-24; Graves, B. J. et al. (1986) Cell, 44, 565-576). FIG. 3 shows that binding of the factors to WT-530/-510 probe is competed out by the excess oligonucleotide having the NF-Y binding sequence (NF-Y, lane 7 and 8). The degree of competition was almost identical to the one with excess probe WT-530/-510 (lane 3 and 4). However, oligonucleotides that had NF-I and CP2 binding sites did not compete effectively (FIG. 3, lane 5, 6, 9, and 10). Moreover, when gel shift assays using the NF-Y probe were conducted, excess amount of WT -530/-510 and NF-Y probe both competed out the binding site with the NF-Y probe, but MUT-530/-510 did not (data not shown). This result indicates that ubiquitously expressed transcription factor NF-Y may bind to the CCAAT box located in the p27$^{Kip1}$ promoter.

Figure 4:
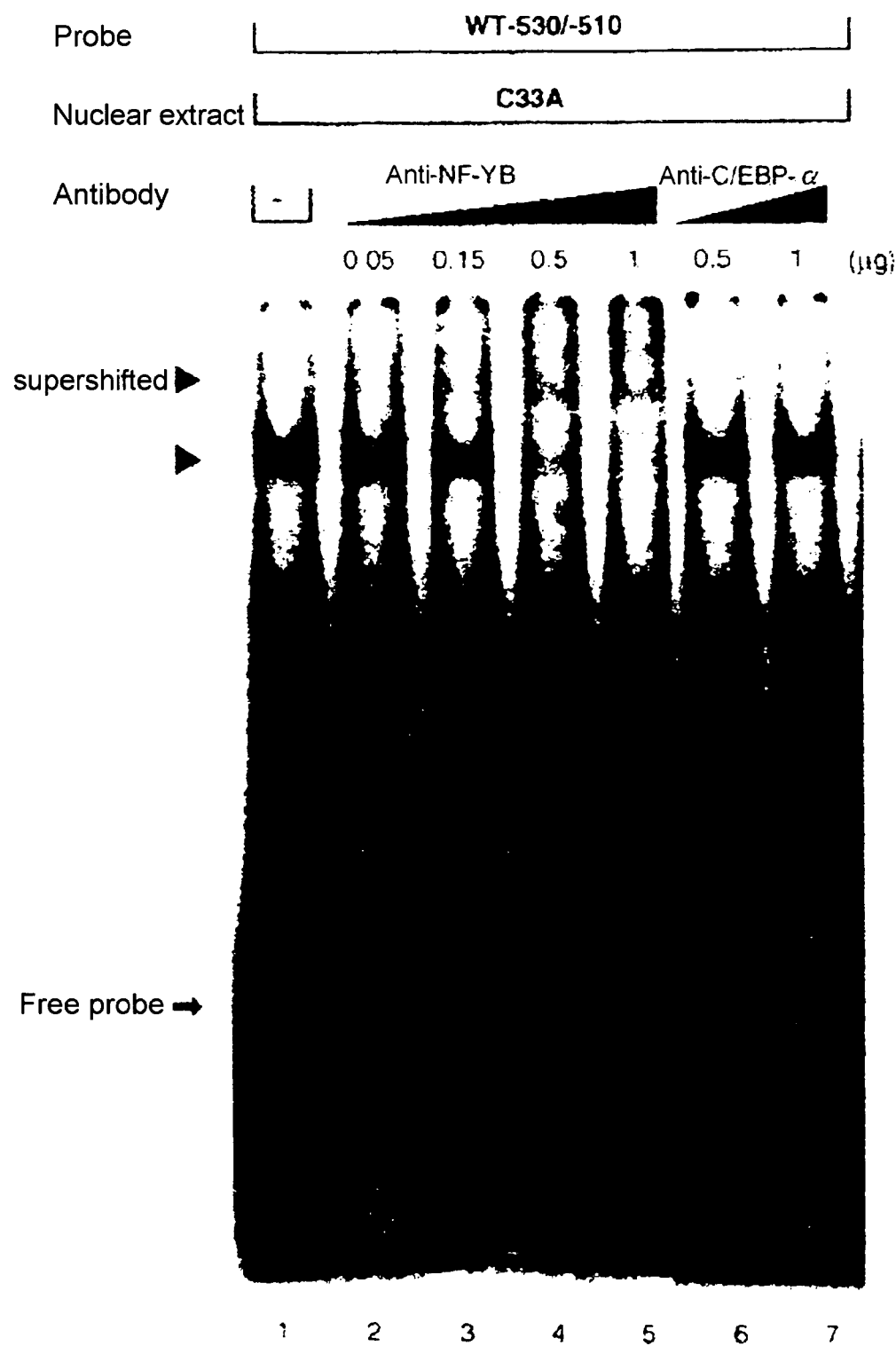
FIG. 4 is a photograph that shows a super shift assay using antibodies. WT-530/−510 was used as a probe. Nuclear extracts were incubated with $^{32}$P-labeled WT-530/−510 in the presence of anti-NF-YB antibody (lane 2-5) or anti-C/EBPa antibody (lane 6 and 7) or in the absence of antibodies (−) (lane 1). The bands that showed a super shift and those that showed a decreased mobility are indicated on the left.

Super shift assays were conducted using antibodies to confirm whether the transcription factor that binds to the WT-530/-510 probe is NF-Y. NF-Y consists of three subunits: NF-YA, NF-YB, and NF-YC. The antibody against the β subunit of NY-Y (Mantovani, R. et al. (1992) EMBO J., 11, 3315-3322; Huang, L. et al. (1994) J. Virol., 68, 2108-2117; Liu, Q. et al. (1998) Circ. Res., 82, 251-260) was used for the assay. Anti-C/EBPα antibody (Landschulz, W. H. et al. (1988) Genes Dev., 2, 786-800) was used as a negative control. As shown in FIG. 4, the complex was super shifted in the presence of anti-NF-YB antibody but anti-C/EBP antibody did not cause the super shift (lane 2-5). These results demonstrated that the NF-Y bound to the CCAAT box located in the p27$^{Kip1}$ promoter.

Figure 5:
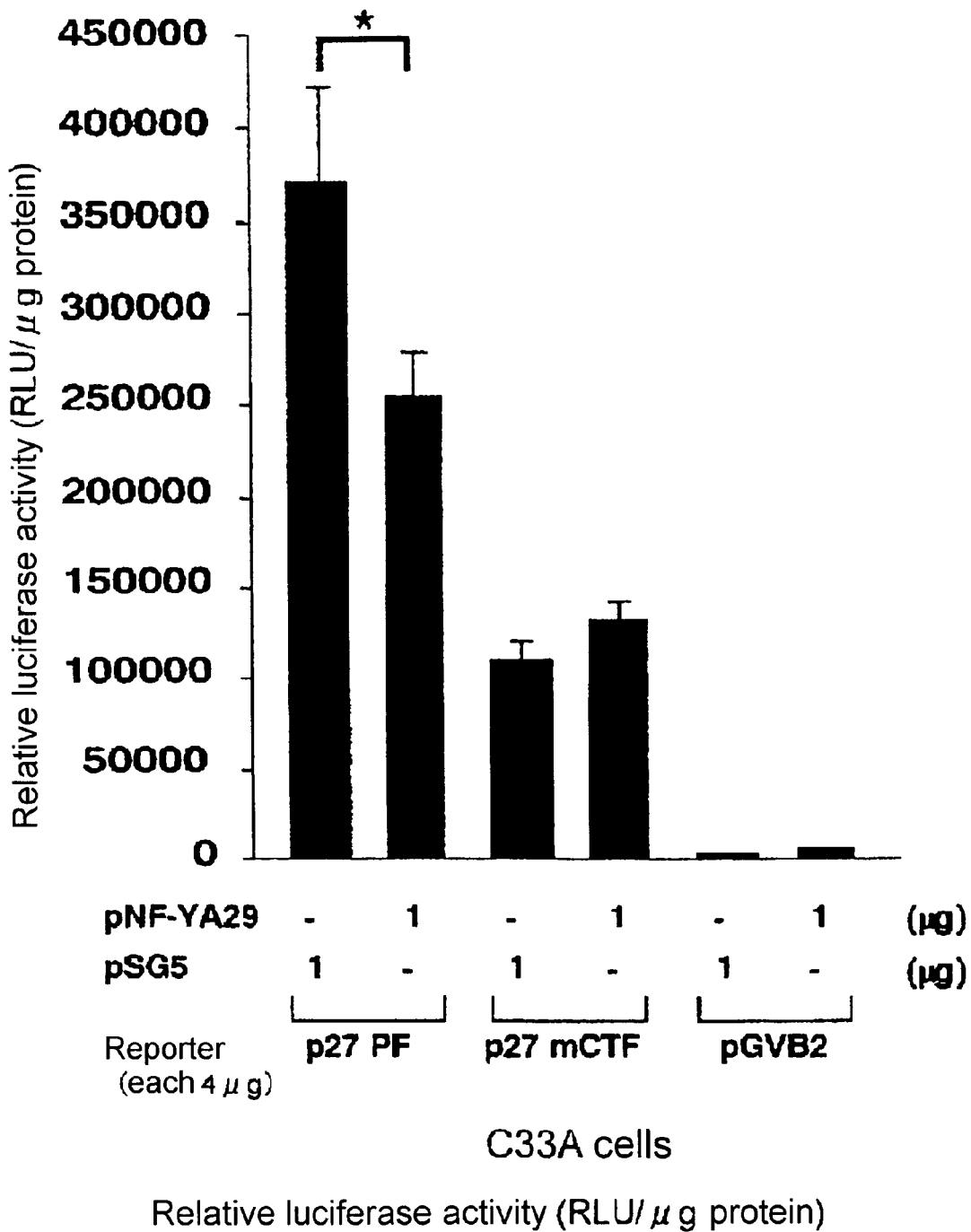
FIG. 5 shows that a dominant negative NF-YA expression plasmid (pNF-YA29) suppresses p27$^{Kip1}$ promoter activity via the CCAAT box. C33A cells were co-transfected with 4 µg of p27PF or p27mCTF, with 1 µg of dominant negative NF-YA expression plasmid (pNF-YA29) or its parental expression vector (pSG5). Luciferase activities were analyzed 24 hrs after transfection. Data shown are means (bars indicate standard deviation) (n=3). *, p<0.05.

A NF-YA dominant negative mutant (pNF-YA29) (Liu, Q. et al. (1998) Circ. Res., 82, 251-260; Mantovani, R, et al. (1994) J. Biol. Chem., 269, 20340-20346; Jackson, S. M. et al. (1995) J. Biol. Chem., 270, 21445-21448) or a parental construct thereof (pSG5) was co-transfected with p27PF or p27mCTF to confirm the involvement of NF-YA in p27$^{Kip1}$ transcription regulation. The NF-Y dominant negative expression plasmid (pNF-YA29) was a gift from Dr. R. Mantovani from the University of Milan. As shown in FIG. 5, luciferase activity of cells carrying p27PF was decreased to about 70% by co-transfection with pNF-YA29. This indicated that NF-Y (at least partially) regulates p27$^{Kip1}$ transcription via the CCAAT box in p27$^{Kip1}$ promoter.

EXAMPLE 3

Vitamin D$_3$ Responsive Elements in the p27$^{Kip1}$ Promoter

It has been reported that p27$^{Kip1}$ and p21$^{Cip1}$ are transcriptionally induced by vitamin D$_3$ (Liu, M. et al. (1996) Genes Dev., 10, 142-153). The present inventors also observed that p27$^{Kip1}$ mRNA was induced after treatment of U937 cells with vitamin D$_3$ and it peaked between 24 h and 48 h (approximately 4-fold compared with 0 h), while p21$^{Cip1}$ mRNA induction was more rapid. This suggests that vitamin D$_3$ regulates transcription of p27$^{Kip1}$ in a VDR/VDRE independent manner unlike the regulation of p21$^{Cip1}$ transcription. To investigate the regulatory mechanisms behind p27$^{Kip1}$ gene expression, the present inventors first investigated the effect of vitamin D$_3$ on the transcriptional activity of the promoter of the p27$^{Kip1}$ gene. Namely, the effect of vitamin D$_3$ on the wild-type p27$^{Kip1}$ promoter-luciferase fusion plasmid, p27PF, was examined by transient transfection.

Transfections into U937 cells were performed as described in literature (Pahl, H. L. et al. (1991) Exp. Hematol., 19, 1038-1041). In brief, cells were electroporated at 250 V, 980 μF (BioRad Gene Pulser; BioRad), incubated for 15 minutes on ice, and then transferred to 20 ml prewarmed RPMI 1640 containing 10% FBS and divided equally into two cultures. They were incubated with either $1\times10^{-7}$ M vitamin D$_3$ (1,25-dihydroxyvitamin D$_3$; vitamin D$_3$ used in Examples 3-6 below refers to "1,25-dihydroxyvitamin D$_3$") or 10 μl of equivalent vehicle (ethanol). Cells were harvested 40 h after treatment and preparation of extracts and the luciferase assay were performed using the Dual-Luciferase Reporter Assay (Promega) according to the manufacturer's instructions. All transfections included a reference sample with pGL2 Basic Vector or PicaGene Promoter Vector 2. For normalization of transfection efficiencies, 2 μg of renilla (renilla; sea pansy) luciferase expression plasmid (pRL-TK, Promega) was included in the transfections. The reporter luciferase activity was calculated by subtracting the intrinsic activity as measured by samples corresponding to the pGL2 Basic Vector or PicaGene Promoter Vector 2 and then normalized to transfection efficiency as measured by the activity from pRL-TK.

Figure 6:
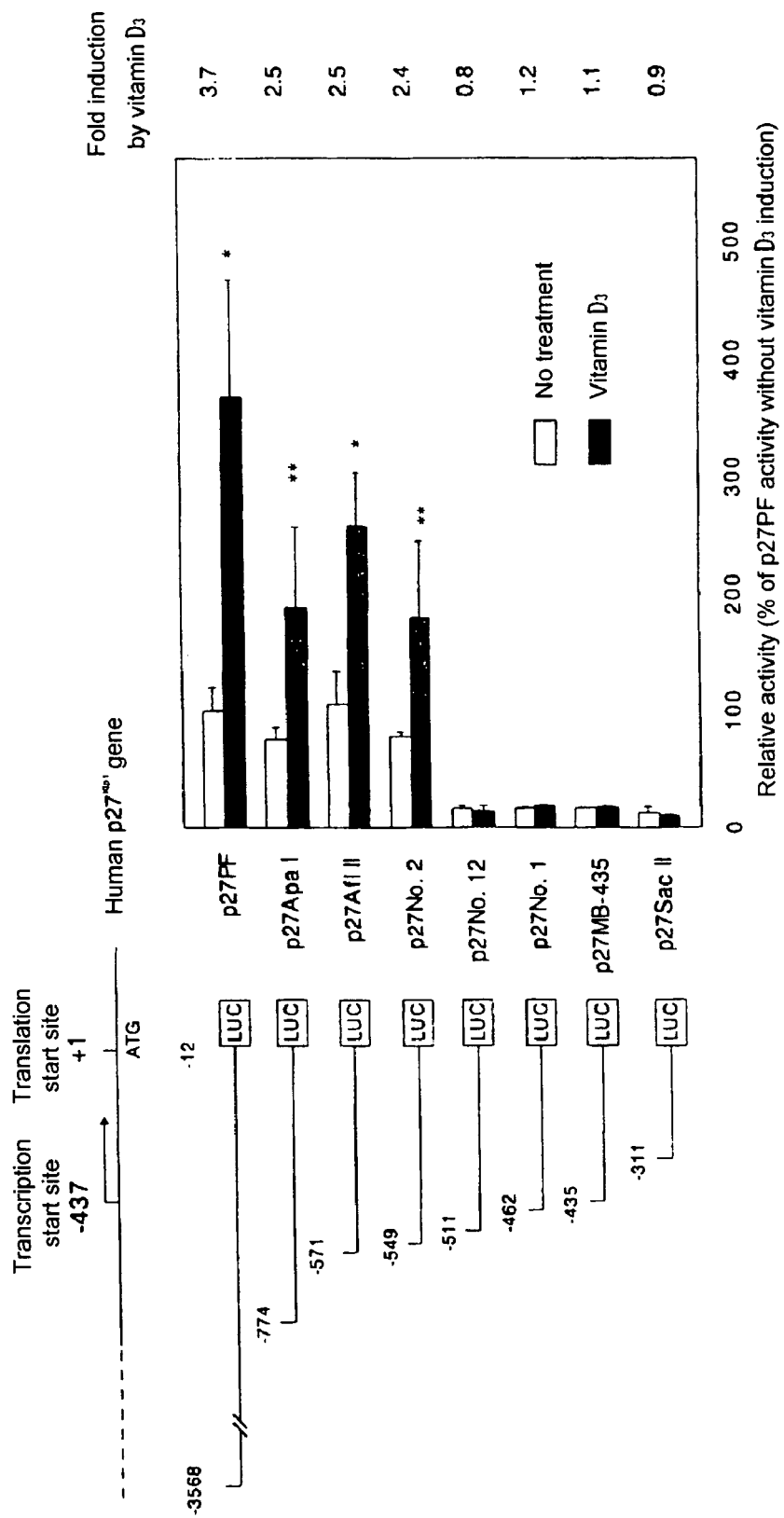
FIG. 6 indicates differential effects of vitamin D$_3$ on human p27$^{Kip1}$ promoter activities using a series of 5'-deletions. Eighteen µg of each constructed plasmid was transiently transfected into U937 cells with 2 µg of pRL-TK, and luciferase activities were analyzed after a 40 h treatment of 10$^{-7}$ M vitamin D$_3$. Relative luciferase activities are shown as percentages of that of p27PF in the absence of vitamin D$_3$. Data are shown as means (bars, standard deviation) (n=3). *, p<0.01; **, p<0.05.

Following a 40 h exposure to vitamin D$_3$, the luciferase activity from the p27PF plasmid increased approximately 3-4 fold as compared to that of the vehicle treated control (FIG. 6). This result was consistent with the inventors' observation of the effect of vitamin D$_3$ on p27$^{Kip1}$ expression by Northern analysis, indicating that this 3.6-kb promoter fragment was necessary and sufficient for the response of p27$^{Kip1}$ gene to vitamin D$_3$. Next, the present inventors tried to determine whether any particular regions in the 3.6-kb fragment were responsive to vitamin D$_3$. For this purpose, a series of 5' deletion constructs of the p27$^{Kip1}$ promoter were examined. FIG. 1 shows that deletion up to position −549 (relative to the translation start site) did not result in significant changes in the response to vitamin D$_3$, and that the responsiveness was completely abolished using deletions up to −511, while deletions up to −311 exhibited some promoter activities in the absence of vitamin D$_3$. These results indicated that potential vitamin D$_3$ regulatory elements appeared to be located between −549 and −511.

Figure 7:
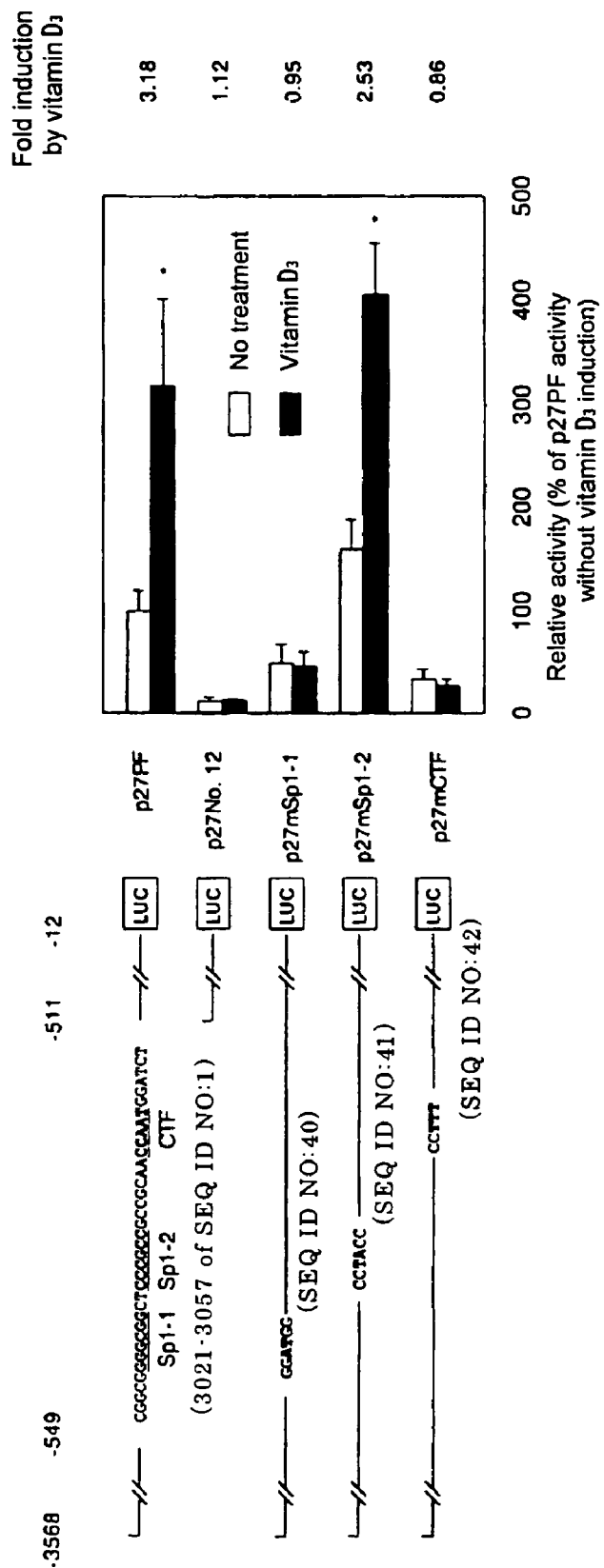
FIG. 7 indicates mutation analysis to identify vitamin D3-responsive sequences in the p27$^{Kip1}$ promoter. The three different mutants (SEQ ID NOS:40-42) shown on the left are identical to the wild type p27PF (nucleotides 3021-3057 of SEQ ID NO:1), except for the mutation indicated in bold letters. Eighteen µg of each constructed plasmid was transiently transfected into U937 cells with 2 µg of PRL-TK. Luciferase activities were analyzed after a 40 h treatment with 10$^{-7}$ M vitamin D$_3$ in comparison to p27PF without vitamin D$_3$ treatment. Data are shown as means (bars indicate standard deviation) (n=3). *, p<0.01.

The region between −549 and −511 harbored two Sp1 sites (−544 and −534) and a CCAAT box (−522) that were adjacent to each other and were conserved between the human and mouse p27$^{Kip1}$ promoters (Minami, S. et al. (1997) FEBS Lett., 411, 1-6; Zhang, Y. and Lin, S. C. (1997) Biochem. Biophys. Acta., 1353, 307-317). As described above, the present inventors termed the two upstream Sp1 sites Sp1-1 and Sp1-2, respectively (FIG. 7). To determine whether the two Sp1 sites and the CCAAT box were involved in activation by vitamin D$_3$, a series of mutants of p27PF, p27mSp1-1, p27mSp1-2, and p27mCTF with mutations in the Sp1-1 site, the Sp1-2 site, or the CCAAT box, respectively, were analyzed (FIG. 7). As shown in FIG. 7, the response to vitamin D$_3$ was abolished using p27mSp1-1 and p27mCTF but not p27mSp1-2. On the other hand, all mutants retained some promoter activities in the absence of vitamin D$_3$. Therefore, the present inventors concluded that at least both the Sp1-1 and the CCAAT box were the vitamin D$_3$-responsive elements and that the Sp1-2 site was not involved in the activation by vitamin D$_3$.

EXAMPLE 4

Figure 8:
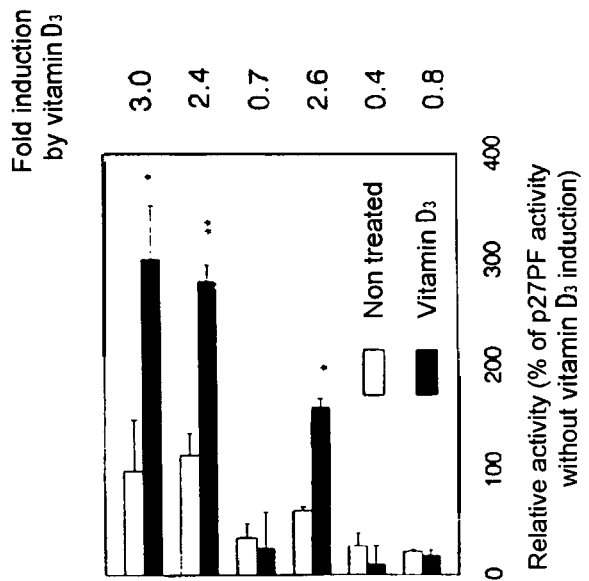
FIG. 8 indicates that the four tandem repeats of a 44 bp regulatory sequence between −555/−512 that contains the Sp1-1 site and the CCAAT box confers vitamin D$_3$ responsiveness to a heterologous promoter. Five constructs, PGPV2 [−555/−512wild]$_4$, PGPV2-[−555/−512 msp1-1]$_4$, PGPV2-[−555/−512 mSp1-2]$_4$, PGPV2-[−555/−512mCTF]$_4$, and PGPV2-[R-555/−512wild]$_4$ were generated as described herein. Eighteen µg of each constructed plasmid was transiently transfected into U937 cells with 2 µg of pRL-TK, and luciferase activities were analyzed after a 40 h treatment with 10$^{-7}$ M vitamin D$_3$ in comparison to p27PF without vitamin D$_3$ treatment. Data are shown as means (bars, standard deviation) (n=3). *, p<0.01; **, p<0.03.
Figure 8:
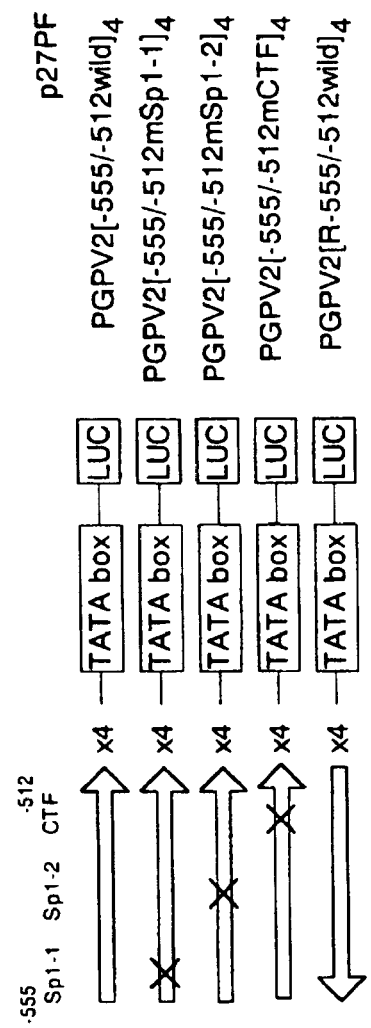

A 44-bp Regulatory Sequence Between −555/−512 that Contains the Sp1-1 Site and the CCAAT Box Confers Response to Vitamin $D_3$ to a Heterologous Promoter To examine vitamin $D_3$ regulation via the Sp1-1-site and the CCAAT box that are located near each other downstream from −555, plasmids, in which four tandem copies of the sequences corresponding to −555/−512 with or without mutations of the Sp1-1 site, the Sp1-2 site, or the CCAAT box were inserted upstream of the SV40 early promoter in the PicaGene Promoter Vector 2 in a normal (PGPV2[−555/−512wild]$_4$, PGPV2[−555/−512 mSp1-1]$_4$, PGPV2[−555/−512 mSp1-2]$_4$, and PGPV2[−555/−512mCTF]$_4$, or a reverse orientation (PGPV2[R−555/−512wild]$_4$), were constructed as above (FIG. 8). As shown in FIG. 8, four copies of the 44 bp fragment corresponding to the region between −555 and −512 of the p27$^{Kip1}$ promoter conferred significant response to vitamin $D_3$ to the SV40 early promoter in an orientation-dependent manner following transient transfection of U937 cells, although one copy of the same fragment did not respond to vitamin $D_3$. Mutations introduced in either the Sp1-1 or the CCAAT box (PGPV2[−555/−512 mSp1-1]$_4$, PGPV2[−555/−512mCTF]$_4$, respectively) abolished any stimulatory effect by vitamin $D_3$, whereas luciferase activity of a construct containing mutations in the Sp1-2 site (PGPV2[−555/−512 mSp1-2]$_4$) was activated by vitamin $D_3$ in a similar manner to p27PF and PGPV2[−555/−512wild]$_4$. The present inventors concluded that the region between −555 and −512 relative to the translation start site (−118 and −75 relative to the transcription start site) was sufficient for vitamin $D_3$-induced transcription of the p27$^{Kip1}$ gene. Furthermore, both the Sp1-1 site and the CCAAT box in this region were vitamin $D_3$-responsive elements and were required for vitamin $D_3$-induced transcription of the p27$^{Kip1}$ gene.

EXAMPLE 5

Identification of Nuclear Proteins Interacting with the Vitamin $D_3$-Responsive Sequence To identify the nuclear factors binding to the vitamin $D_3$-responsive sequence, a set of oligonucleotides spanning −555 to −512 was used as a probe for gel shift assays (−555/−512wild, see Table 1). Nuclear extracts were prepared from U937 cells treated with vitamin $D_3$ for 36 h and gel shift assay was carried out as follows.

Nuclear extracts of U937 cells were prepared according to the procedure of Andrew and Faller (Andrews, N. C. and Faller, D. V. (1991) Nucleic Acids Res., 19, 2499). The cells were treated with either $1\times10^{-7}$ M vitamin $D_3$ or vehicle for 36 h before extraction. Gel shift assays were carried out as described by Orita et al. (Orita, T. et al. (1997) J. Biol. Chem., 272, 23216-23223). The reaction mixture for the gel shift assay (25 μl final volume) contained 20 mM Tris-HCl (pH 8.0), 100 mM KCl, 10% glycerol, 1 μg of poly(dI-dC), and 2 μg of nuclear extract. After preincubation for 15 minutes at 23° C., probe DNA (approximately 0.5 ng, 10,000 cpm) was added to the mixture, and the binding reaction was allowed to proceed at 23° C. for 20 min. The resulting product was then resolved by electrophoresis on 4% acrylamide-bisacrylamide (29:1), 0.5×TBE nondenaturing gel at 10 V/cm for 150 min. Competition analyses were performed by mixing the indicated amount of appropriate competitor DNA to the binding reaction prior to addition of nuclear extracts. In supershift experiments, antibodies against Sp1 (sc-59X; Santa Cruz), Sp3 (sc-644X; Santa Cruz), and C/EBP-α (sc-7204X; Santa Cruz) were purchased. The antibodies against NF-YA, -YB, and -YC (IgG fraction) were kindly provided by Drs. T. Orita and S. Nagata of Osaka University Medical School. These antibodies were added to the incubation mixture containing nuclear protein before addition of probe DNA.

Figure 9:
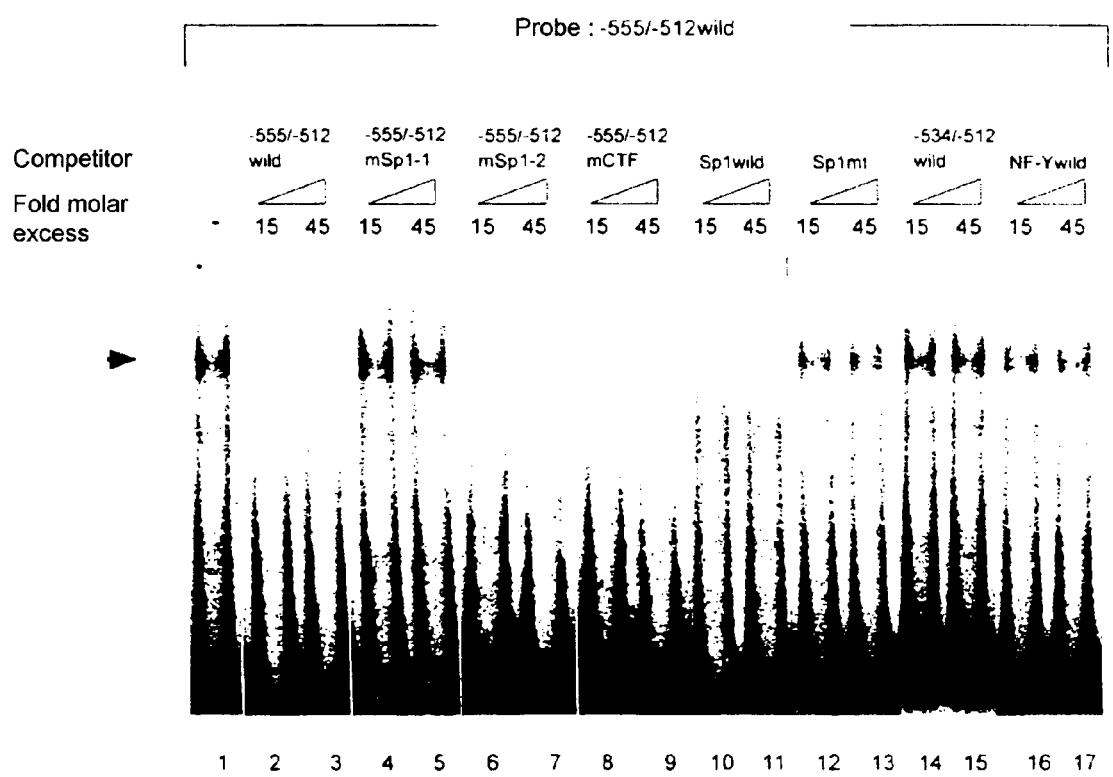
FIG. 9 is a photograph showing the result of gel shift assays carried out with nuclear extracts prepared from vitamin D$_3$-treated U937 cells. A set of oligonucleotides containing the Sp1-1 and CTF sites between −555 and −512 (−555/−512wild) was used as a probe. Nuclear extracts were incubated with 32p-labeled −555/−512wild in the absence (−) (lane 1) or in the presence of 15- or 45-fold amounts of various unlabeled oligonucleotides.
Figure 10:
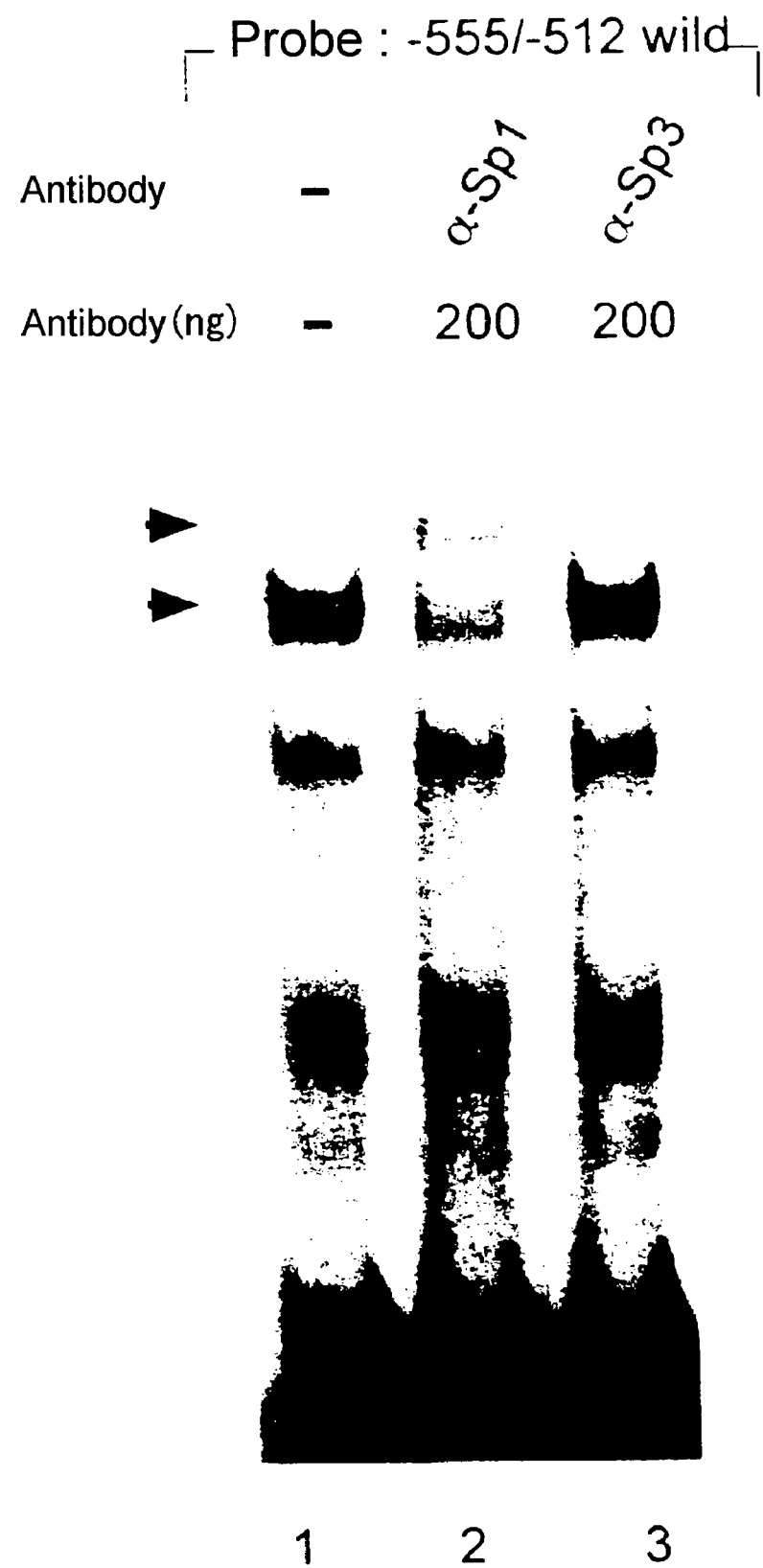
FIG. 10 is a photograph showing that Sp1 can interact with one of the vitamin D$_3$ responsive sequences, Sp1-1 site. Shows effects of anti-Sp1 and anti-Sp3 antibodies on the formation of the complexes. Complexes were formed in the absence (lane 1) or in the presence of anti-Sp1 (lane 2) or anti-Sp3 antibodies (lane 3).

As shown in FIG. 9, the oligonucleotides −555/−512wild yielded a single major retarded band (lane 1), which was competed out by an excess of unlabeled oligonucleotide (lanes 2 and 3). To localize the sequence that binds to nuclear factor(s), a series of oligonucleotides that carried point mutations in the Sp1-1, the Sp1-2, or the CCAAT box (−555/−512 mSp1-1, −555/−512 mSp1-2, and −555/−512mCTF, respectively), oligonucleotides carrying wild type or a mutated sequence for the sequence Sp1 site or CCAAT box (Sp1wild, Sp1mt, and NF-Ywild) and oligonucleotides spanning −534 to −512 (−534/−511) were used as competitors. As shown in lanes 4-17, the retarded band was not competed out by the addition of −555/−512 mSp1-1, Sp1mt, NF-Ywild, or −534/−512wild, indicating that Sp1 family protein(s) bind to the Sp1-1 site. To elucidate whether the retarded band represents the binding of Sp1 or Sp3, gel shift assays were performed with nuclear extracts that were preincubated with anti-Sp1 or -Sp3 antibody for band supershift experiments (Nakano, K. et al. (1997) J. Biol. Chem., 272, 22199-22206). As shown in FIG. 10, in the presence of anti-Sp1 antibody, but not anti-Sp3 antibody, the complex was supershifted. Thus, the present inventors concluded that Sp1 binds to the Sp1-1 site of the vitamin $D_3$ regulatory region of the p27$^{Kip1}$ promoter in U937 cells.

Figure 11:
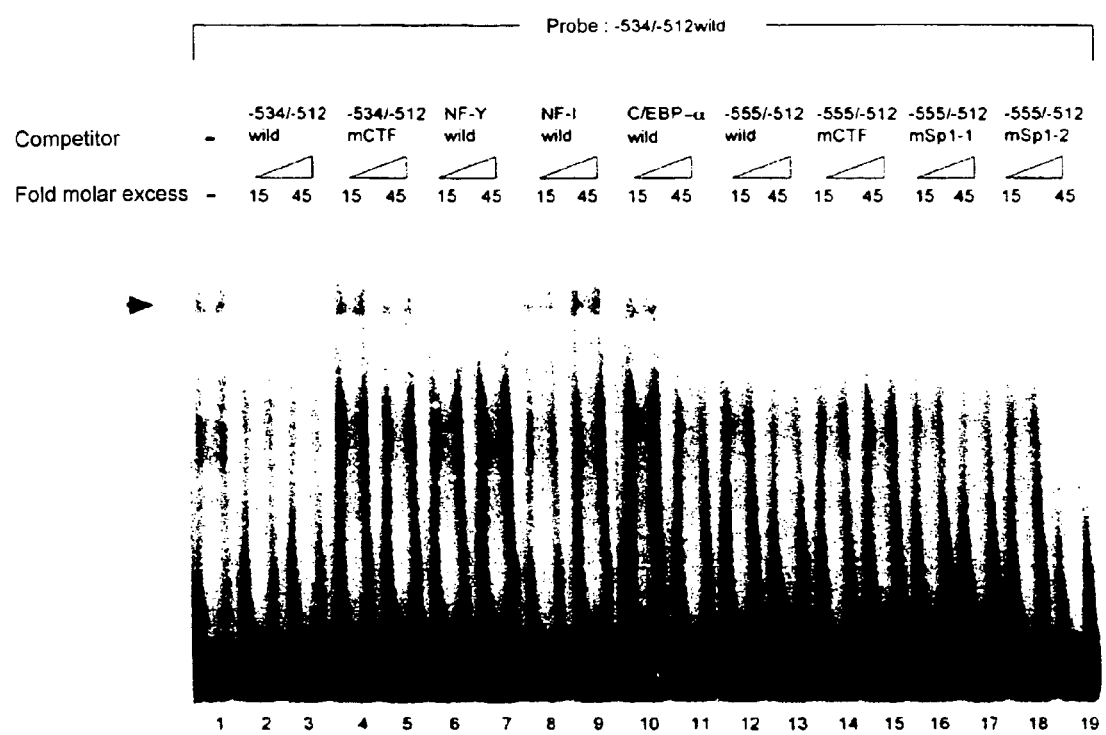
FIG. 11 is a photograph showing the result of gel shift assays carried out with nuclear extracts prepared from vitamin D$_3$-treated U937 cells. A set of oligonucleotides containing the CTF site between −534 and −512 (−534/−512wild) was used as a probe. Nuclear extracts were incubated with $^{32}$P-labeled −534/−512wild in the absence (lane 1) or in the presence of 15- or 45-fold amounts of various unlabeled oligonucleotides.

The present inventors also analyzed the sequence between −534 and −512 (that carries the CCAAT box) but not the Sp1-1 and Spt-2 sites. A set of oligonucleotides spanning this region was used for gel shift assays. As shown in FIG. 11, the present inventors observed a single major retarded band, which was competed out by excess unlabeled wild type oligonucleotides (−534/−512wild), but not those carrying a mutation in the CCAAT box (−534/−512mCTF) (lanes 1-5). This indicated that nuclear factor(s) bind to the CCAAT box of the p27$^{Kip1}$ promoter. So far, it has been reported that several different transcriptional factors including NF-Y, C/EBP, CBP, and NF-I are capable of binding to CCAAT box (Dorn, A. et al. (1987) Cell, 50, 863-872; Graves, B. J. et al. (1986) Cell, 44, 565-576; Hooft van Huijsduijnen, R. A. et al., (1987) Nucleic Acids Res., 15, 7265-7282; Chodosh, L. A. et al. (1988) Cell, 53, 11-24).

To elucidate which transcription factor binds to the CCAAT box in the regulatory region of the p27$^{Kip1}$ promoter, the present inventors performed competition experiments using unlabeled oligonucleotides carrying the CCAAT box that had been reported to bind to NF-Y, C/EBP-α, or NF-I with high affinity (NF-Ywild, C/EBP-αwild, and NF-Iwild, respectively). As shown in FIG. 11, the retarded band was competed by the addition of NF-Ywild, but not NF-Iwild, or C/EBP-αwild. This suggested that NF-Y binds to this CTF Site.

Figure 12:
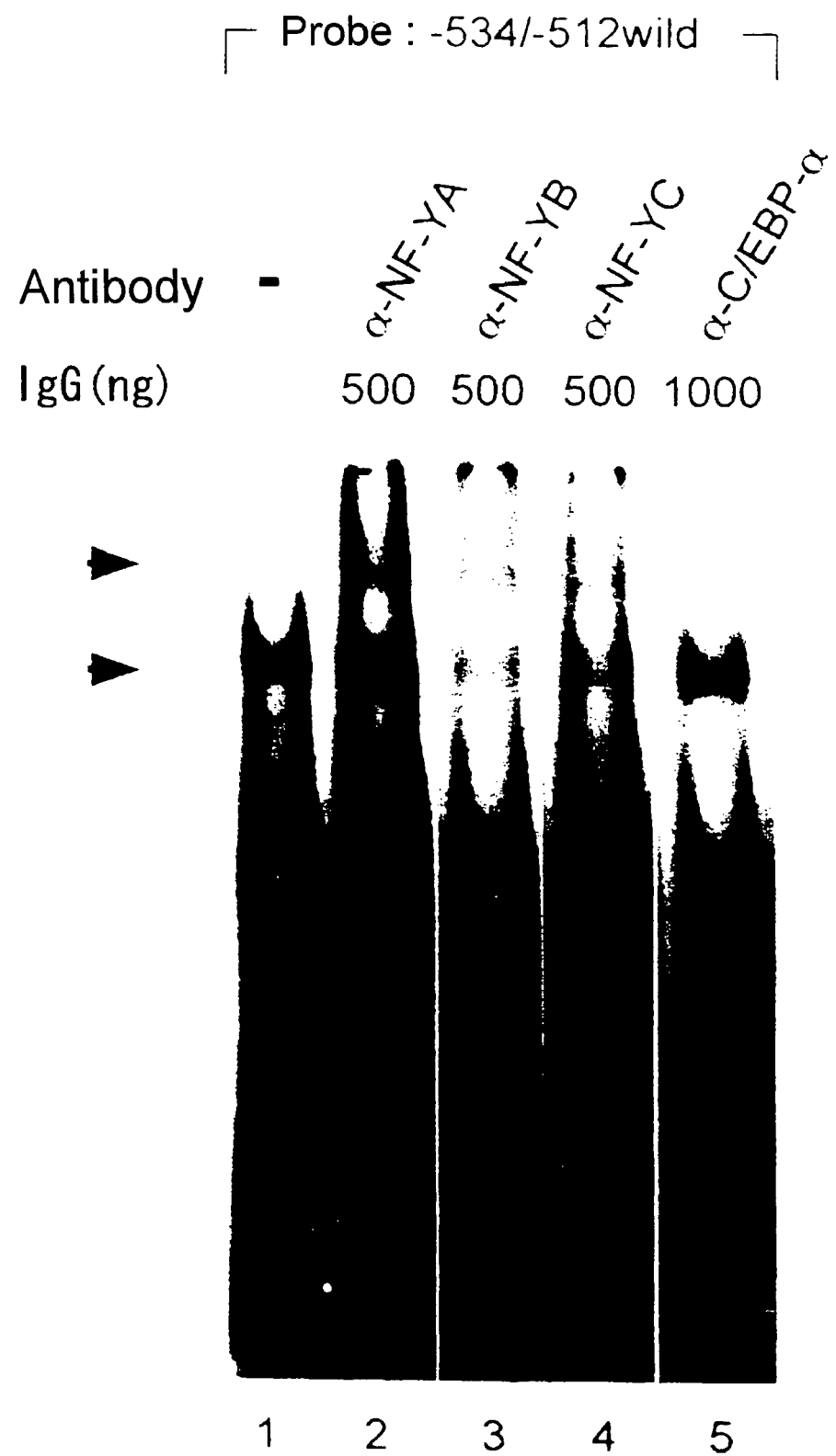
FIG. 12 is a photograph indicating that NF-Y can interact with another vitamin D$_3$ responsive sequence, CTF site. Effects of anti-NF-Y and anti-C/EBP-α antibodies on the formation of the complexes. Complexes were formed in the absence (lane 1) or in the presence of anti-NF-YA, -YB, or YC antibodies (lanes 2-4) or anti-C/EBP-α antibody (lane 5).

To confirm this result, the present inventors performed supershift assays using anti-NF-Y antibodies. NF-Y is composed of three subunits, NF-YA, NF-YB, and NF-YC. The present inventors used anti-NF-YA, -B, and -YC antibodies (Orita, T. et al. (1997) J. Biol. Chem., 272, 23216-23223; Mantovani, R. et al. (1992) EMBO J., 11, 3315-3322) and anti-C/EBP-α antibody for supershift experiments. As shown in FIG. 12, in the presence of anti-NF-YA, -YB or -YC antibodies, the complex was supershifted. The addition of anti-C/EBP-α did not affect the complex. These results demonstrated that trimeric NF-Y binds to the CCAAT box of the regulatory region of the p27$^{Kip1}$ promoter.

To verify that NF-Y could bind not only to the CCAAT box in the −534/−512wild sequence but also to the site in the −555/−512 wild sequence, the present inventors again used oligonucleotides spanning −555 to −512, with or without mutations in Sp1-1, Sp1-2, or CTF site as competitors. For the same purpose, the present inventors investigated the effects of the addition of anti-NF-YA, -YB, or -YC antibodies on the formation of the complexes of −555/512 wild probe and nuclear proteins by gel shift assays. The addition of anti-NF-YA, -YB, or -YC antibody did not affect the complexes of −555/−512wild and nuclear proteins. However, as shown in FIG. 11, NF-Y binding to the probe −534/−512wild was competed by −555/−512wild, −555/−512 mSp1-1, and −555/−512 mSp1-2, although these oligonucleotides were less effective than −534/−512wild, while NF-Y binding to −534/−512wild was not affected by −555/−512mCTF. These results indicated that NF-Y binds to the CCAAT box in −555/−512wild as well as the site in −534/−512wild. Therefore, the present inventors concluded that Sp1 and NF-Y bind to the Sp1-1 site and the CCAAT box, respectively, the regulatory elements that are required for vitamin D$_3$-induced transcription of the p27$^{Kip1}$ gene.

Figure 13:
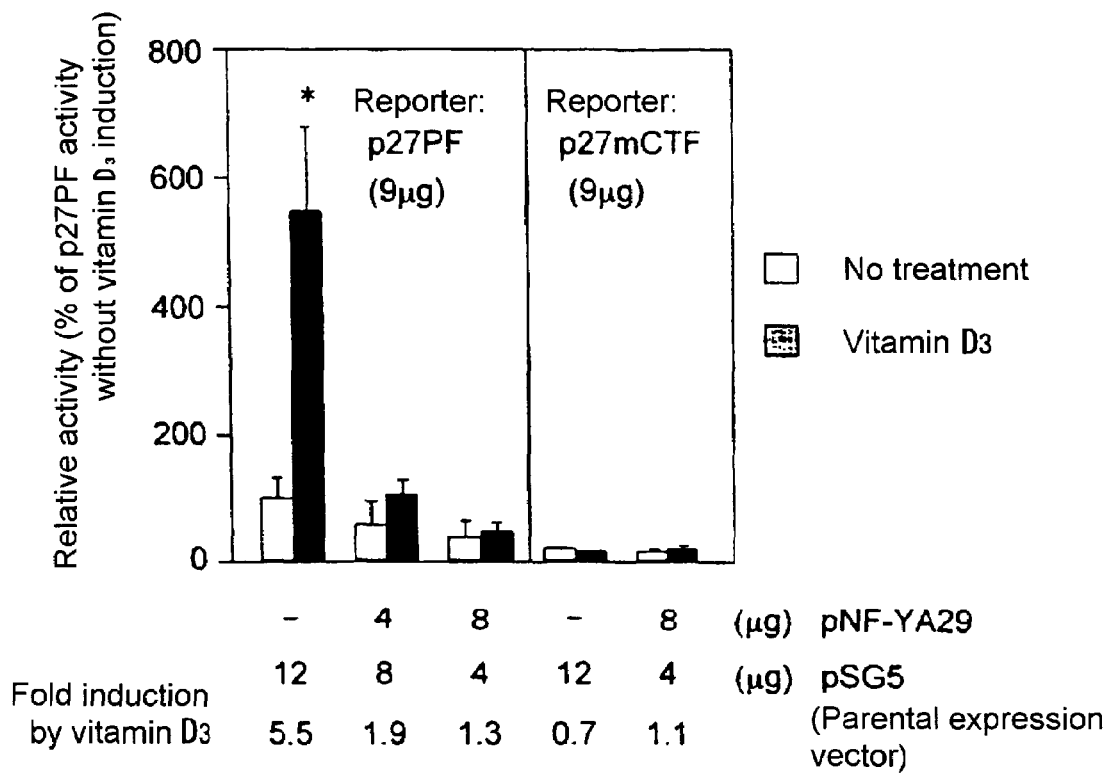
FIG. 13 shows that a dominant-negative NF-YA expression plasmid (pNF-YA29) suppresses the vitamin D$_3$ responsiveness of p27 promoter. Nine µg of p27PF or p27mCTF was co-transfected into U937 cells with various amounts of expression plasmid for the dominant negative NF-YA (pNF-YA29) with 2 µg of pRL-TK. Luciferase activities were analyzed after a 40 hr treatment with 10$^{-7}$ M vitamin D$_3$ in comparison to p27PF without vitamin D$_3$ treatment. Data are shown as means (bars, standard deviation) (n=3). *, p<0.01.

To further confirm the involvement of NF-Y in the vitamin D$_3$-induced transcription of p27$^{Kip1}$, the present inventors' cotransfected p27PF or p27mCTF with a dominant negative NF-YA mutant expression plasmid (pNF-YA29) (Mantovani, R. et al. (1994) J. Biol. Chem., 269, 20340-20346). As shown in FIG. 13, pNF-YA29 suppressed the vitamin D$_3$-induced luciferase activities from p27PF but not p27mCTF in a dose-dependent manner. This result directly demonstrates that NF-Y mediates the up-regulation of p27$^{Kip1}$ transcription by vitamin D$_3$ via the CTF site of its promoter.

EXAMPLE 6

Analysis of Sp1 and NF-Y Subunits after Vitamin D$_3$ Treatment

Figure 14:
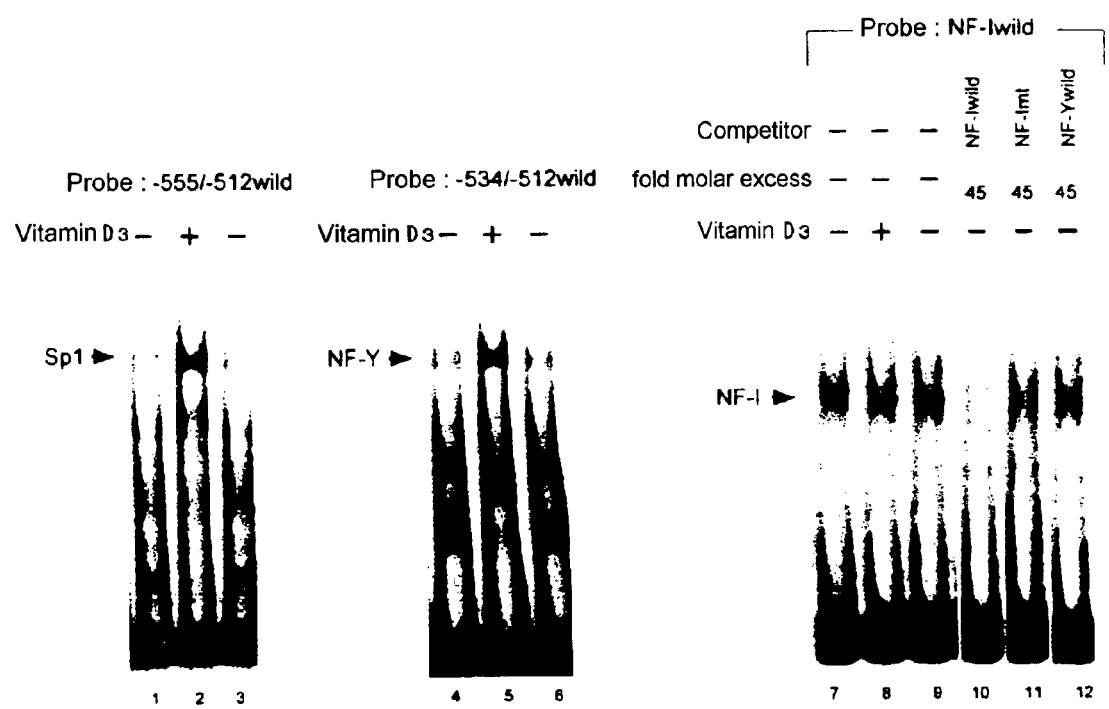
FIG. 14 is a photograph indicating showing the change of Sp1 and NF-Y binding activities to the p27$^{Kip1}$ promoter after vitamin D$_3$ treatment. Nuclear extracts were prepared from either vitamin D$_3$ treated or vehicle (ethanol) treated U937 cells for 36 h. Two µg of each nuclear extract was incubated with the −555/−512wild probe (lanes 1-3), −534/−512wild probe (lanes 4-6), or NF-Iwild probe (lanes 7-12) to detect Sp1, NF-Y, and NF-I, respectively.

The results described above strongly suggested that Sp1 and NF-Y are the essential regulators of vitamin D$_3$-induced transcription of the p27$^{Kip1}$ gene. To investigate the mechanism as to how Sp1 and NF-Y regulate transcription of the p27$^{Kip1}$ gene, the present inventors examined whether binding of Sp1 and NF-Y to the p27$^{Kip1}$ promoter was altered following vitamin D$_3$ treatment, using gel shift assays similar to those in Example 5. Nuclear extracts were prepared from U937 cells treated with either vitamin D$_3$ or vehicle alone for 36 h. As a probe, −555/−512 wild oligonucleotides or −534/−512 wild oligonucleotides were used to detect Sp1 and NF-Y, respectively. As shown in FIG. 14, the present inventors observed that Sp1 and NF-Y binding activities increased significantly after vitamin D$_3$ treatment. Because the DNA binding activity of an unrelated transcription factor (i.e., NF-I) was not changed by the treatment of vitamin D$_3$, the present inventors concluded that the treatment of vitamin D$_3$ specifically stimulates the binding of Sp1 and NF-Y to the p27$^{Kip1}$ promoter.

To analyze the protein levels of Sp1 and NF-Y subunits, U937 cells treated with vitamin D$_3$ or vehicle alone at different time points were collected, and whole cell extracts were then prepared from the cells. The amounts of these proteins were analyzed by Western Blotting.

After vitamin D$_3$ treatment, collected cells (3×10$^7$) were washed in cold PBS twice and then resuspended in 150 μl of lysis buffer (50 mM Tris-HCl [pH 7.9], 150 mM NaCl, 0.1% SDS, 0.5% deoxycholate, 1% Nonidet P-40, 10% glycerol, 0.2 mM PMSF, and 10 μg/ml aprotinin). This was subjected to mild sonication and used as whole cell extracts. Extracts (from 1×10$^6$ cells) were subjected to 12% SDS-PAGE and blotted onto polyvinylidene difluoride membranes (PVDF membrane; Millipore). The membranes were incubated with the primary antibodies and then incubated with horseradish peroxidase-conjugated secondary antibody. The resulting immune complexes were visualized using an enhanced chemiluminescence system (ECL; Amersham). The antibodies against NF-YA, -YB, and -YC and the antibody against Sp1 (sc-59; Santa Cruz) were used at a 1:1000 and 1:200 dilution in blocking buffer (3% milk powder in PBS), respectively.

Figure 15:
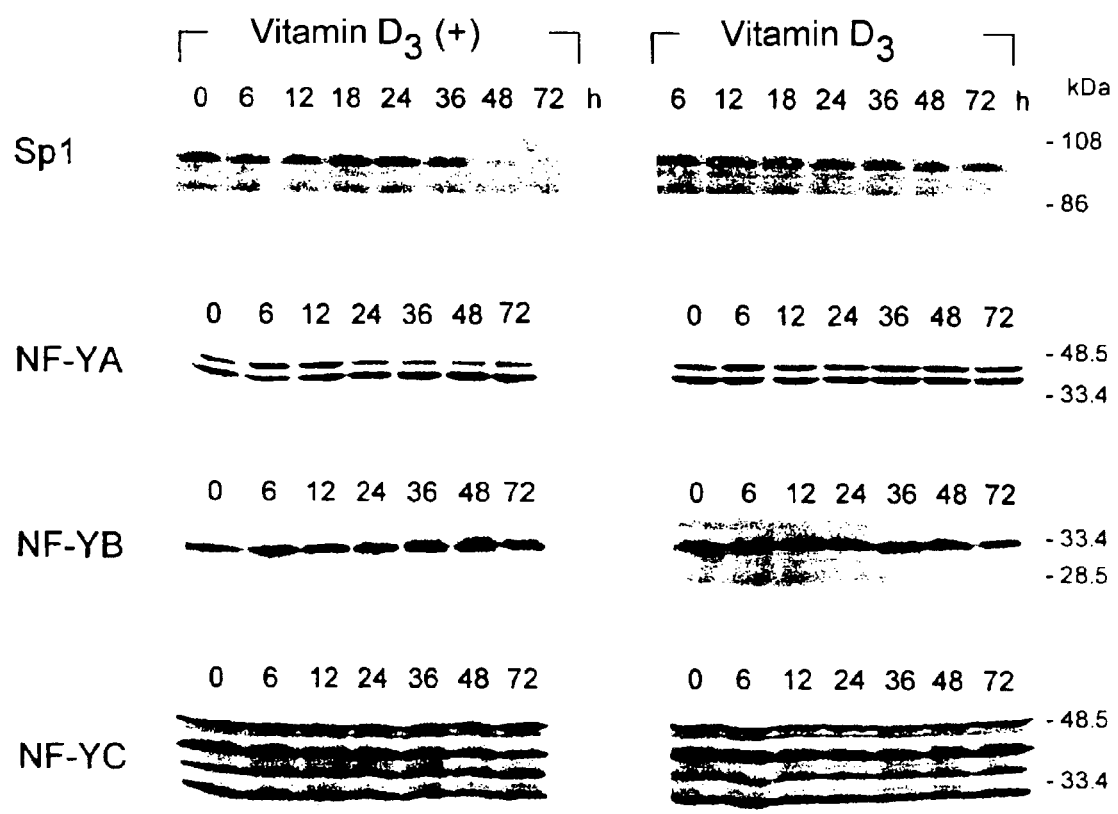
FIG. 15 is a photograph indicating a change of Sp1 and NF-Y subunits after vitamin D$_3$ treatment. Whole cell extracts were prepared from U937 cells at the indicated time points after the treatment of vitamin $D_3$. Extracts were subjected to 12% SDS-PAGE, followed by Western Blotting with anti-Sp1 or with anti-NF-YA, -YB, -YC antibodies.

As shown in FIG. 15, the level of Sp1 increased slightly from 12 h to 18 h after the vitamin D$_3$ treatment, after 36 h the level of Sp1 was reduced and barely detectable. The increase in the level of Sp1 occurred prior to the increase of p27$^{Kip1}$ mRNA following vitamin D$_3$ treatment. Interestingly the level of Sp1 protein showed little difference between vitamin D$_3$ and vehicle-treated cells after 36 h, when the present inventors could observe a significant increase in the binding of Sp1 to the Sp1-1 site of the human p27$^{Kip1}$ promoter (FIG. 14). These results indicate that post-translational regulation of Sp1 such as phosphorylation (Jackson, S. P. et al. (1990) Cell, 63, 155-165) and glycosylation (Jackson, S. P. and Tjian, R., (1988) Cell, 55, 125-133) could contribute to up-regulation of p27$^{Kip1}$ transcription by vitamin D$_3$ in combination with slight induction of Sp1 protein. On the other hand, as reported previously, the present inventors also observed two bands for NF-YA (36 kDa and 39 kDa) that were thought to result from differential splicing (Orita, T. et al. (1997) J. Biol. Chem., 272, 23216-23223; Li, X. Y. et al. (1992) J. Biol. Chem., 267, 8984-8990; Ishimaru, F. et al. (1997) Blood, 89, 4136-4145) (FIG. 15). To our surprise, the level of the 39-kDa form of NF-YA decreased from 12 h to 48 h after the vitamin D$_3$ treatment. To confirm that this change resulted from the decrease of long form NF-YA mRNA, the present inventors performed RT-PCR analysis of NF-YA mRNA using primers F1 and R that were located in the regions that are conserved in the two isoforms.

RT-PCR of NF-YA mRNA was carried out as follows. Total RNA was prepared using the TRIZOL™ (Gibco-BRL)/chloroform method from U937 cells treated with either 10$^{-7}$ M vitamin D$_3$ or vehicle at different time points. RT-PCR was performed using the RNA PCR Kit Ver. 2.1 (Takara, Tokyo, Japan). The forward (F) and reverse (R) primers for NF-YA-short and -long were AATAGTTCGACAGAGCAGATTG (Primer F1) (SEQ ID NO: 12), CCTCCTGAT-TGGGTTTCGGAGT (primer F2) (SEQ ID NO: 13), and GGGGTTAGGACACTCGGATGAT (primer R) (SEQ ID NO: 14). The forward and reverse primers for G3PDH were ACCACAGTCCATGCCTCA (SEQ ID NO: 15) and TCCACCACCCTGTTGCTGTA (SEQ ID NO: 16). One microgram of total RNA was used for RT-PCR. PCR was performed for 25 and 20 cycles to detect NF-YA subunits and G3PDH, respectively. PCR products were subjected to electrophoresis in a 3% agarose gel. The primers for NF-YA were designed to detect two different isoforms simultaneously and were located in regions that were conserved in the two isoforms (Li, X. Y. et al. (1992) J. Biol. Chem., 267, 8984-8990).

Figure 16:
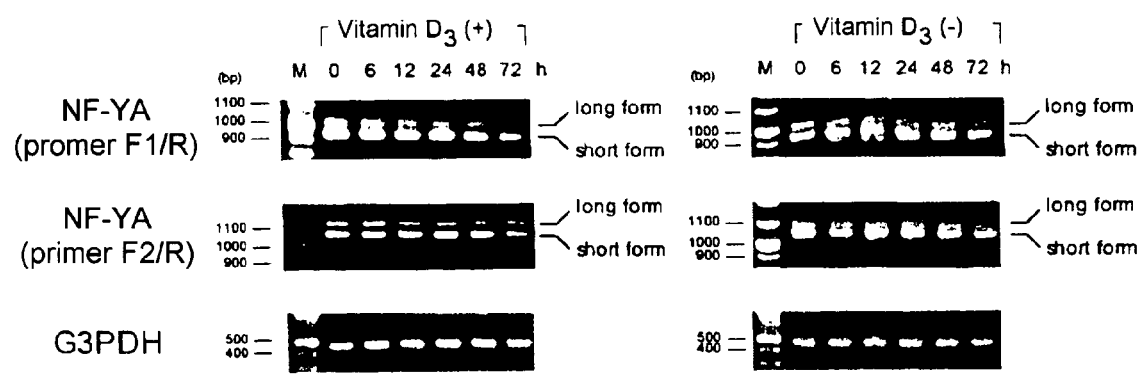
FIG. 16 is a photograph indicating a change of Sp1 and NF-Y subunits after vitamin $D_3$ treatment. Total RNAs were prepared from U937 cells at the indicated time after the treatment of vitamin $D_3$. RT-PCR was carried out using different combinations of PCR primers. Primers F1 and R (top panel); Primers F2 and R (middle panel); Primers for G3PDH (bottom panel).

As shown in FIG. 16, the present inventors obtained two bands that were derived from two isoforms of NF-YA mRNA judging from restriction enzyme analysis (data not shown). As expected, the long form of NF-YA decreased gradually in vitamin D$_3$-treated cells. The same results were obtained with a different combination of PCR primers (primer F2 and R). These results suggested that a decrease of the band for 39 kDa NF-YA protein resulted from the decrease of its mRNA and not protein modification. This decrease in high-molecular-weight form of NF-YA was observed prior to the increase of p27$^{Kip1}$ mRNA after vitamin D$_3$ treatment. A significant change was not seen in the level of NF-YB and NF-YC between vitamin $D_3$ and vehicle treated cells (FIG. 15). Taken together, these results suggest that NF-Y acts as a mediator of vitamin $D_3$ in the regulation of p27$^{Kip1}$ transcription via the decrease in high-molecular-weight form of NF-YA.

INDUSTRIAL APPLICABILITY

This invention provides vitamin-$D_3$ responsive sequences located in the 5' regulatory region of the p27$^{Kip1}$ gene. The vitamin $D_3$-responsive sequences of the present invention can be used for vitamin $D_3$-dependent expression of any gene. In addition, the sequences can be used in the screening for pharmaceutical agents that regulate p27$^{Kip1}$ gene expression. The screening methods using the vitamin $D_3$-responsive sequences of the present invention would enable screening of highly specific pharmaceutical agents compared to screening using the longer p27$^{Kip1}$ promoter region.

The invention claimed is:

1. An isolated DNA having the activity to give positive vitamin $D_3$ responsiveness to heterologous and homologous promoters, wherein said DNA is selected from the group consisting of:
   (a) an isolated DNA consisting of the nucleotide sequence from position 3014 to position 3057 of SEQ ID NO: 1;
   (b) an isolated DNA consisting of the nucleotide sequence from position 3014 to position 3057 of SEQ ID NO: 1, which has been modified by a substitution, deletion, addition, and/or insertion of one or two nucleotides; and
   (c) an isolated DNA consisting of three to five tandem copies of the nucleotide sequence of the DNA of (a) or (b).

2. A vector comprising the DNA of claim 1, wherein said vector does not comprise a DNA consisting of the nucleotide sequence from position 2795 to position 3134 of SEQ ID NO: 1.

3. The vector of claim 2, further comprising a reporter gene operably linked downstream of said isolated DNA.

4. A cell comprising the vector of claims 2 or 3.

5. A method of screening for a compound that regulates the expression of the $p27^{Kip1}$ gene, wherein said method comprises the steps of:
   (a) contacting a test sample to a cell comprising the vector of claim 3;
   (b) detecting reporter activity in said cell; and
   (c) selecting a compound that increases or decreases the reporter activity when compared to the activity in the absence of said test sample.

6. A vector comprising an isolated DNA consisting of the nucleotide sequence from position 3014 to position 3057 of SEQ ID NO: 1, wherein said vector does not comprise a DNA consisting of the nucleotide sequence from position 2795 to position 3134 of SEQ ID NO: 1.

7. The vector of claim 6, further comprising a reporter gene operably linked downstream of said isolated DNA.

8. A cell comprising the vector of claims 6 or 7.

9. A vector comprising an isolated DNA consisting of the nucleotide sequence from position 3014 to position 3057 of SEQ ID NO: 1, wherein said nucleotide sequence has been modified by a substitution, deletion, addition, and/or insertion of one or two nucleotides, and wherein said vector does not comprise a DNA consisting of the nucleotide sequence from position 2795 to position 3134 of SEQ ID NO: 1.

10. The vector of claim 9, further comprising a reporter gene operably linked downstream of said isolated DNA.

11. A cell comprising the vector of claims 9 or 10.

12. A vector comprising an isolated DNA consisting of three to five tandem copies of the nucleotide sequence from position 3014 to position 3057 of SEQ ID NO: 1.

13. The vector of claim 12, further comprising a reporter gene operably linked downstream of said isolated DNA.

14. A cell comprising the vector of claims 12 or 13.

* * * * *

UNITED STATES PATENT AND TRADEMARK OFFICE
CERTIFICATE OF CORRECTION

| | | |
|---|---|---|
| PATENT NO. | : 7,465,541 B1 | Page 1 of 1 |
| APPLICATION NO. | : 10/181614 | |
| DATED | : December 16, 2008 | |
| INVENTOR(S) | : Toshiyuki Sakai et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 341 days.

should read (*) Notice: Subject to any disclaimer, the term of this patent is extended or adjusted under 35 U.S.C. 154(b) by 583 days.

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO.        : 7,465,541 B1
APPLICATION NO.   : 10/181614
DATED             : December 16, 2008
INVENTOR(S)       : Toshiyuki Sakai Page 1 of 1

It is certified that error appears in the above-identified patent and that said Letters Patent is hereby corrected as shown below:

On the Title Page, Item (54) and Col. 1 line 1-5 in the Title, replace "OF P27$^{KIP1}$" with --OF THE P27$^{KIP1}$--.

On the Title Page, Item (73), under Assignees, replace "Chungai" with --Chugai--.

Column 3, Line 15, replace "(-545/-538)" with --(-543/-538)--.

Column 11, Line 64, replace "D3-responsive" with --D$_3$-responsive--.

Column 12, Line 2, replace "PRL-TK." with --pRL-TK.--.

Signed and Sealed this
Fourteenth Day of August, 2012

David J. Kappos
*Director of the United States Patent and Trademark Office*

SEQUENCE LISTING

```
<160> NUMBER OF SEQ ID NOS: 42

<210> SEQ ID NO 1
<211> LENGTH: 3568
<212> TYPE: DNA
<213> ORGANISM: Homo sapiens

<400> SEQUENCE: 1
ctcgaggaag gactgaaact gtgtgcttgc ggtgggaggg gcagctgggc aaggaaccgt      60
gaaccttcgc agaaacattt ggggctgcag aacttgggtg agagcgctgc atctgggagc     120
tggcgacgct ggcggcttgc tcattcaccc catctgaaca cttgtctatg acacaggtgt     180
tttctcttaa gttatttggg tctttgcctc tctcctcagg ttgtgaagat tacagaaatc     240
tgggatggct tatgggacgc ttctcagccc taagtaggaa aacagcagtg aaaatggcaa     300
ccaaaacatc acgcaggact gggggttttg gggaaacagc tcactttaga gcagtgcagt     360
gtagagcttt ccgtcttcta ccagggtcca cctttaacac tgtttatctg aaaattttcc     420
ccctggctta ctcgcttgca gctgcccact ttgcagaagg atggcgctct gatctctacg     480
ctccctgttc cttcagggac tccatagtat ttttttcac gcgtcgtcgc tactacagca     540
gacgcctgcg ttctcattat ttgctgtaca gatctccggt gccttgactg taaacaaaac     600
actttagatc attgtgaggt cgatgtaagc acagcctttc tgctggcagc cagacttctt     660
aaggtggtgt gactgtgact tgcttacttt tcgagatcaa caacaacaaa gcgacaaaat     720
ggtgctccta catattagtt gaaagattca gcatgtgaag gggatcgaag tgtttatttt     780
ccacttccat ataagacatg aattccatga gtaaaatcaa cttctgtggc aaggtgaact     840
actctagaat gtctccattt acatacatgt ggtagtttgg atgtttatgc atatggatag     900
atgcacatat atagagttcc tgtgttgtct agcaattgtt ttaaaatttg gacaattatc     960
taatttctag ggtaaggtat aaattatggt agggaggcct accctaattt tcctgttcct    1020
tttcccccag tctgcagtcc aataaattga cagccttaaa agtagaaaaa ctaaagagga    1080
tgagacctct tgcttgatcc taggtgaatt cttttctgtc agttaggtag gaagtcctga    1140
cttgaaaact agttctgggc actgccccct ttactgttct ctgggtatca acccctgtcc    1200 ttcaattta gttgaactag tggatggtga taccacaggc tcaagacagc tgcatttaaa    1260
tatcagtgac cacaggccac atcaaggaaa catctgcagg caacccaggg cctgggaagg    1320
agccatttca gtcacttgta agacagcagg acctgcagac tacagcacaa tcaaactcag    1380
acaaaaccct gaaccagtga gaaccattag gaaggaaagg aacagaaaat gaaccaacct    1440
gagtgttagg agacttgcat ctagtcctga ctccggtacc aaccgaatgc atgtccctgg    1500
acaggaaacc tctctgagtc tcgatttcct ccgtggtaaa aaggagaggg ttaaaccaca    1560
gggtcccgag ggtcccttcc agctgtcaca ttctggagcg tatgagatga ggtaggcaca    1620
caaagtggac aagatgtggc taagaaaaca agctacacat caagctcatc tgtagcatag    1680
```

```
gtgcttaaga aaactttgct gctgtgtaat attagaacgg aaggttggtt tccagtaaaa    1740
tgcattaact ttggctcaaa ccaagatgat gggtaccggg catggggtg gggaggcagt     1800 tgaagatcca ctgagctttg tctcagggca gccctgctca tcgtcctact ttaccttcca    1860
ccacggtgct caagcccaca ctgagagaga aatttccagc tgcaaaaggg agaagagaaa    1920
cgctggaata ctagtatcgg acgttaggac atggttgtgg tgttttaaaa atcatttcat    1980
catctggagt ttgaccccga ggggagtatt ttcacccttc agccctctga aagcattcac    2040
tagcatctga atattgttct gagtttgttg gagcagtgaa atctggtgag agagaagggt    2100
ggaggaagga aggagctgtt gtatttggcg gctggactca ggtagaggaa actgctacaa    2160
tcccgggaaa gaacagaaaa gtagaaaggg acgagttccc acacgcagcc aatgtccatg    2220
gccttaactg tgcttgggaa ggaagatcct gggccagggg tgtaccctcg ttttcaaaa     2280 actaaacgtg tctgagacag ctacaaagtt tattaaggga cttgagagac tagagttttt    2340 tgttttttt ttttaatctt gagttccttt cttatttca ttgagggaga gcttgagttc      2400
atgataagtg ccgcgtctac tcctggctaa tttctaaaag aaagacgttc gctttggctt    2460
cttccctagg cccccagcct ccccagggat ggcagaaact tctgggttaa ggctgagcga    2520
accattgccc actgcctcca ccagccccca gcaaaggcac gccggcgggg gggcgcccag    2580
cccccccagc aaacgctccg cggcctcccc cgcagaccac gaggtggggg ccgctgggga    2640
gggccgagct gggggcagct cgccaccccg gctcctagcg agctgccggc gaccttcgcg    2700
gtcctctggt ccaggtcccg gcttcccggg agaggagcgg gagggaggtc ggggcttagg    2760
cgccgctgcg aacccgccaa cgcagcgccg ggccccgaac ctcaggcccc gccccaggtt    2820
cccggccgtt tggctagttt gtttgtctta attttaattt ctccgaggcc agccagagca    2880
ggtttgttgg cagcagtacc cctccagcag tcacgcgacc agccaatctc ccggcggcgc    2940
tcggggaggc ggcgcgctcg ggaacgaggg gaggtggcgg aaccgcgccg gggccacctt    3000
aaggccgcgc tcgccagcct cggcggggcg gctcccgccg ccgcaaccaa tggatctcct    3060
cctctgttta aatagactcg ccgtgtcaat cattttcttc ttcgtcagcc tcccttccac    3120
cgccatattg ggccactaaa aaaggggggc tcgtcttttc ggggtgtttt tctcccctc     3180 ccctgtcccc gcttgctcac ggctctgcga ctccgacgcc ggcaaggttt ggagagcggc    3240
tgggttcgcg ggaccgcggg cttgcacccg cccagactcg gacgggcttt gccaccctct    3300
ccgcttgcct ggtcccctct cctctccgcc ctcccgctcg ccagtccatt tgatcagcgg    3360
agactcggcg gccgggccgg ggcttccccg cagcccctgc gcgctcctag agctcgggcc    3420
gtggctcgtc ggggtctgtg tcttttggct ccgagggcag tcgctgggct tccgagaggg    3480
ggttcgggcc gcgtaggggc gctttgtttt gttcggtttt gtttttttga gagtgcgaga    3540
gaggcggtcg tgcagacccg ggagaaag                                       3568
```

<210> SEQ ID NO 2
<211> LENGTH: 26
<212> TYPE: DNA
<213> ORGANISM: Artificial
<220> FEATURE:
<223> OTHER INFORMATION: Artificially Synthesized Oligonucleotide
      Sequence

<400> SEQUENCE: 2
cagcctcggc gggatggctc ccgccg                                         26

```
<210> SEQ ID NO 3
<211> LENGTH: 29
<212> TYPE: DNA
<213> ORGANISM: Artificial
<220> FEATURE:
<223> OTHER INFORMATION: Artificially Synthesized Oligonucleotide
      Sequence

<400> SEQUENCE: 3
cggggcggct cctaccgccg caaccaatg                                              29

<210> SEQ ID NO 4
<211> LENGTH: 26
<212> TYPE: DNA
<213> ORGANISM: Artificial
<220> FEATURE:
<223> OTHER INFORMATION: Artificially Synthesized Oligonucleotide
      Sequence

<400> SEQUENCE: 4
gccgccgcaa cctttggatc tcctcc                                                 26

<210> SEQ ID NO 5
<211> LENGTH: 48
<212> TYPE: DNA
<213> ORGANISM: Artificial
<220> FEATURE:
<223> OTHER INFORMATION: Artificially Synthesized Oligonucleotide
      Sequence

<400> SEQUENCE: 5
agggagcctc ggcggggcgg ctcccgccgc cgcaaccaat ggatctcc                         48

<210> SEQ ID NO 6
<211> LENGTH: 48
<212> TYPE: DNA
<213> ORGANISM: Artificial
<220> FEATURE:
<223> OTHER INFORMATION: Artificially Synthesized Oligonucleotide
      Sequence

<400> SEQUENCE: 6
ccctggagat ccattggttg cggcggcggg agccgccccg ccgaggct                         48

<210> SEQ ID NO 7
<211> LENGTH: 25
<212> TYPE: DNA
<213> ORGANISM: Artificial
<220> FEATURE:
<223> OTHER INFORMATION: Artificially Synthesized Oligonucleotide
      Sequence

<400> SEQUENCE: 7
ctagcgccgc aaccaatgga tctcc                                                  25

<210> SEQ ID NO 8
<211> LENGTH: 25
<212> TYPE: DNA
<213> ORGANISM: Artificial
<220> FEATURE:
<223> OTHER INFORMATION: Artificially Synthesized Oligonucleotide
      Sequence

<400> SEQUENCE: 8
ctagcgccgc aacctttgga tctcc                                                  25

<210> SEQ ID NO 9
```

```
<211> LENGTH: 29
<212> TYPE: DNA
<213> ORGANISM: Artificial
<220> FEATURE:
<223> OTHER INFORMATION: Artificially Synthesized Oligonucleotide
      Sequence

<400> SEQUENCE: 9
ctagttttgg attgaagcca atatgataa                                            29

<210> SEQ ID NO 10
<211> LENGTH: 26
<212> TYPE: DNA
<213> ORGANISM: Artificial
<220> FEATURE:
<223> OTHER INFORMATION: Artificially Synthesized Oligonucleotide
      Sequence

<400> SEQUENCE: 10
acttttaacc aatcagaaaa atctag                                               26

<210> SEQ ID NO 11
<211> LENGTH: 27
<212> TYPE: DNA
<213> ORGANISM: Artificial
<220> FEATURE:
<223> OTHER INFORMATION: Artificially Synthesized Oligonucleotide
      Sequence

<400> SEQUENCE: 11
ctagtgacca gttccagcca ctcttta                                              27

<210> SEQ ID NO 12
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 12
aatagttcga cagagcagat tg                                                   22

<210> SEQ ID NO 13
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 13
cctcctgatt gggtttcgga gt                                                   22

<210> SEQ ID NO 14
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 14
ggggttagga cactcggatg at                                                   22

<210> SEQ ID NO 15
<211> LENGTH: 18
```

```
<212> TYPE: DNA
<213> ORGANISM: Artificial
<220> FEATURE:
<223> OTHER INFORMATION: Artificially Synthesized Oligonucleotide
      Sequence

<400> SEQUENCE: 15
accacagtcc atgcctca                                                 18

<210> SEQ ID NO 16
<211> LENGTH: 20
<212> TYPE: DNA
<213> ORGANISM: Artificial
<220> FEATURE:
<223> OTHER INFORMATION: Artificially Synthesized Oligonucleotide
      Sequence

<400> SEQUENCE: 16
tccaccaccc tgttgctgta                                               20

<210> SEQ ID NO 17
<211> LENGTH: 15
<212> TYPE: PRT
<213> ORGANISM: Homo sapiens

<400> SEQUENCE: 17

Arg Gly Lys Thr Cys Ala Asn Asn Asn Arg Gly Lys Thr Cys Ala
1               5                   10                  15

<210> SEQ ID NO 18
<211> LENGTH: 48
<212> TYPE: DNA
<213> ORGANISM: Artificial
<220> FEATURE:
<223> OTHER INFORMATION: Artificially Synthesized Oligonucleotide
      Sequence

<400> SEQUENCE: 18
agggagcctc ggcgggatgg ctcccgccgc cgcaaccaat ggatctcc                48

<210> SEQ ID NO 19
<211> LENGTH: 48
<212> TYPE: DNA
<213> ORGANISM: Artificial
<220> FEATURE:
<223> OTHER INFORMATION: Artificially Synthesized Oligonucleotide
      Sequence

<400> SEQUENCE: 19
ccctggagat ccattggttg cggcggcggg agccatcccg ccgaggct                48

<210> SEQ ID NO 20
<211> LENGTH: 48
<212> TYPE: DNA
<213> ORGANISM: Artificial
<220> FEATURE:
<223> OTHER INFORMATION: Artificially Synthesized Oligonucleotide
      Sequence

<400> SEQUENCE: 20
agggagcctc ggcggggcgg ctcctaccgc cgcaaccaat ggatctcc                48

<210> SEQ ID NO 21
<211> LENGTH: 48
<212> TYPE: DNA
<213> ORGANISM: Artificial
<220> FEATURE:
```

```
<223> OTHER INFORMATION: Artificially Synthesized Oligonucleotide
      Sequence

<400> SEQUENCE: 21
ccctggagat ccattggttg cggcggtagg agccgcccg ccgaggct                    48

<210> SEQ ID NO 22
<211> LENGTH: 48
<212> TYPE: DNA
<213> ORGANISM: Artificial
<220> FEATURE:
<223> OTHER INFORMATION: Artificially Synthesized Oligonucleotide
      Sequence

<400> SEQUENCE: 22
agggagcctc ggcggggcgg ctcccgccgc cgcaaccttt ggatctcc                   48

<210> SEQ ID NO 23
<211> LENGTH: 48
<212> TYPE: DNA
<213> ORGANISM: Artificial
<220> FEATURE:
<223> OTHER INFORMATION: Artificially Synthesized Oligonucleotide
      Sequence

<400> SEQUENCE: 23
ccctggagat ccaaaggttg cggcggcggg agccgcccg ccgaggct                    48

<210> SEQ ID NO 24
<211> LENGTH: 21
<212> TYPE: DNA
<213> ORGANISM: Artificial
<220> FEATURE:
<223> OTHER INFORMATION: Artificially Synthesized Oligonucleotide
      Sequence

<400> SEQUENCE: 24
cgccgcaacc aatggatctc c                                                21

<210> SEQ ID NO 25
<211> LENGTH: 21
<212> TYPE: DNA
<213> ORGANISM: Artificial
<220> FEATURE:
<223> OTHER INFORMATION: Artificially Synthesized Oligonucleotide
      Sequence

<400> SEQUENCE: 25
cgccgcaacc tttggatctc c                                                21

<210> SEQ ID NO 26
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 26
attcgatcgg ggcggggcga gc                                               22

<210> SEQ ID NO 27
<211> LENGTH: 22
<212> TYPE: DNA
<213> ORGANISM: Artificial
<220> FEATURE:
<223> OTHER INFORMATION: Artificially Synthesized Oligonucleotide
```

Sequence

<400> SEQUENCE: 27
attcgatcgg gatggggcga gc                                              22

<210> SEQ ID NO 28
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 28
acttttaacc aatcagaaaa at                                              22

<210> SEQ ID NO 29
<211> LENGTH: 33
<212> TYPE: DNA
<213> ORGANISM: Artificial
<220> FEATURE:
<223> OTHER INFORMATION: Artificially Synthesized Oligonucleotide
      Sequence

<400> SEQUENCE: 29
ctagtacctt atttgaacta accaatcagt tcg                                  33

<210> SEQ ID NO 30
<211> LENGTH: 25
<212> TYPE: DNA
<213> ORGANISM: Artificial
<220> FEATURE:
<223> OTHER INFORMATION: Artificially Synthesized Oligonucleotide
      Sequence

<400> SEQUENCE: 30
ttttggattg aagccaatat gataa                                           25

<210> SEQ ID NO 31
<211> LENGTH: 25
<212> TYPE: DNA
<213> ORGANISM: Artificial
<220> FEATURE:
<223> OTHER INFORMATION: Artificially Synthesized Oligonucleotide
      Sequence

<400> SEQUENCE: 31
ttttggattg aagcctttat gataa                                           25

<210> SEQ ID NO 32
<211> LENGTH: 21
<212> TYPE: DNA
<213> ORGANISM: Artificial
<220> FEATURE:
<223> OTHER INFORMATION: Artificially Synthesized Oligonucleotide
      Sequence

<400> SEQUENCE: 32
ggagatccat tggttgcggc g                                               21

<210> SEQ ID NO 33
<211> LENGTH: 21
<212> TYPE: DNA
<213> ORGANISM: Artificial
<220> FEATURE:
<223> OTHER INFORMATION: Artificially Synthesized Oligonucleotide
      Sequence

```
<400> SEQUENCE: 33
ggagatccaa aggttgcggc g                                               21

<210> SEQ ID NO 34
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 34
cctcgccccg ccccgatcga at                                              22

<210> SEQ ID NO 35
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 35
cctcgcccca tcccgatcga at                                              22

<210> SEQ ID NO 36
<211> LENGTH: 22
<212> TYPE: DNA
<213> ORGANISM: Artificial
<220> FEATURE:
<223> OTHER INFORMATION: Artificially Synthesized Oligonucleotide
      Sequence

<400> SEQUENCE: 36
atttttctga ttggttaaaa gt                                              22

<210> SEQ ID NO 37
<211> LENGTH: 33
<212> TYPE: DNA
<213> ORGANISM: Artificial
<220> FEATURE:
<223> OTHER INFORMATION: Artificially Synthesized Oligonucleotide
      Sequence

<400> SEQUENCE: 37
cgaactgatt ggttagttca ataaggtac tag                                   33

<210> SEQ ID NO 38
<211> LENGTH: 25
<212> TYPE: DNA
<213> ORGANISM: Artificial
<220> FEATURE:
<223> OTHER INFORMATION: Artificially Synthesized Oligonucleotide
      Sequence

<400> SEQUENCE: 38
ttatcatatt ggcttcaatc caaaa                                           25

<210> SEQ ID NO 39
<211> LENGTH: 25
<212> TYPE: DNA
<213> ORGANISM: Artificial
<220> FEATURE:
<223> OTHER INFORMATION: Artificially Synthesized Oligonucleotide
      Sequence
```

```
<400> SEQUENCE: 39
ttatcataaa ggcttcaatc caaaa                                             25

<210> SEQ ID NO 40
<211> LENGTH: 37
<212> TYPE: DNA
<213> ORGANISM: Homo sapiens

<400> SEQUENCE: 40
cggcgggatg gctcccgccg ccgcaaccaa tggatct                                37

<210> SEQ ID NO 41
<211> LENGTH: 37
<212> TYPE: DNA
<213> ORGANISM: Homo sapiens

<400> SEQUENCE: 41
cggcggggcg gctcctaccg ccgcaaccaa tggatct                                37

<210> SEQ ID NO 42
<211> LENGTH: 37
<212> TYPE: DNA
<213> ORGANISM: Homo sapiens

<400> SEQUENCE: 42
cggcggggcg gctcccgccg ccgcaacctt tggatct                                37
```